(12) United States Patent
Lebrun et al.

(10) Patent No.: US 12,115,147 B2
(45) Date of Patent: Oct. 15, 2024

(54) FORMULATIONS AND METHODS RELATED TO EYE IRRITATION

(71) Applicants: Stewart Lebrun, Anaheim, CA (US); Roxanne Chan, Malibu, CA (US); Sara Chavez, Irvine, CA (US)

(72) Inventors: Stewart Lebrun, Anaheim, CA (US); Roxanne Chan, Malibu, CA (US); Sara Chavez, Irvine, CA (US)

(73) Assignee: Lebrun Labs LLC, Anaheim, CA (US)

( * ) Notice: Subject to any disclaimer, the term of this patent is extended or adjusted under 35 U.S.C. 154(b) by 328 days.

(21) Appl. No.: 17/203,467

(22) Filed: Mar. 16, 2021

(65) Prior Publication Data

US 2022/0000838 A1 Jan. 6, 2022

Related U.S. Application Data

(60) Provisional application No. 63/048,112, filed on Jul. 4, 2020.

(51) Int. Cl.
| | |
|---|---|
| *A61K 31/375* | (2006.01) |
| *A61K 47/02* | (2006.01) |
| *A61K 47/36* | (2006.01) |
| *A61K 47/42* | (2017.01) |
| *A61P 27/02* | (2006.01) |
| *A61P 39/06* | (2006.01) |
| *G01N 33/50* | (2006.01) |

(52) U.S. Cl.
CPC ............ *A61K 31/375* (2013.01); *A61K 47/02* (2013.01); *A61K 47/36* (2013.01); *A61K 47/42* (2013.01); *A61P 27/02* (2018.01); *A61P 39/06* (2018.01); *G01N 33/502* (2013.01); *G01N 33/5058* (2013.01); *G01N 33/5088* (2013.01)

(58) Field of Classification Search
CPC ...... A61K 31/375; A61K 47/02; A61K 47/36; A61K 47/42; A61P 27/02; A61P 39/06; G01N 33/502; G01N 33/5058; G01N 33/5088

See application file for complete search history.

(56) References Cited

PUBLICATIONS

Osborne et al (Year: 1995).*
Savian (Year: 2015).*
Vinardell (Year: 2008).*
Jester (Year: 2010).*
Cirillo (Year: 2011).*

* cited by examiner

*Primary Examiner* — Jeffrey S Lundgren
*Assistant Examiner* — Ibrahim D Bori
(74) *Attorney, Agent, or Firm* — Amster, Rothstein & Ebenstein LLP

(57) ABSTRACT

The disclosure relates to formulations and methods for the in vitro testing of ocular irritants. It was discovered that adding an antioxidant formulation to in vitro ocular irritation tests, including for example, a biochemical ocular irritation test, a reconstituted human corneal epithelium (RhCE) ocular irritation test and an excised eye depth of injury (DoI) test, substantially reduces the rate of false positives without diminishing test sensitivity, resulting in more accurately predicting ocular irritancy of test substances. More particularly, the disclosed method employs relatively high physiologic concentrations of one or more antioxidants that are normally present in tears. In a variation, much higher concentrations of one or more antioxidants may provide protection against in vivo exposure to ocular irritants.

5 Claims, 10 Drawing Sheets

| 4A. | Without L-Ascorbic Acid | With L-Ascorbic acid |
|---|---|---|
| n-Hexyl bromide<br>CASRN 111-25-1<br>Nonirritant<br>(GHS Classification NC: Not classified as an Ocular Irritant) | Region of Dead Cells | Region of Live Cells |

| 4B. | Without L-Ascorbic Acid | With L-Ascorbic Acid |
|---|---|---|
| Dioctyl ether<br>CASRN 629-82-3<br>Nonirritant<br>(GHS Classification NC: Not classified as an Ocular Irritant) | Region of Live Cells | Region of Live Cells |

| 4C. | Without L-Ascorbic Acid | With L-Ascorbic Acid |
|---|---|---|
| Isopropyl myristae<br>CASRN 110-27-0<br>Nonirritant<br>(GHS Classification NC: Not classified as an Ocular Irritant) | Region of Live Cells | Region of Live Cells |

FIGS. 4A-4C

| 4D. | Without L-Ascorbic Acid | With L-Ascorbic acid |
|---|---|---|
| Methyl acetate<br>CASRN 79-20-9<br>Irritant<br>(GHS Classification Category 2) | 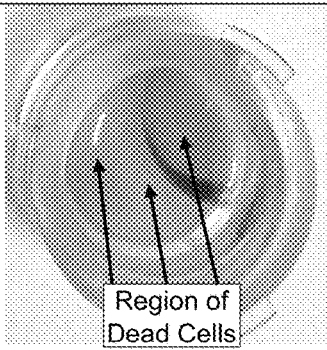<br>Region of Dead Cells | 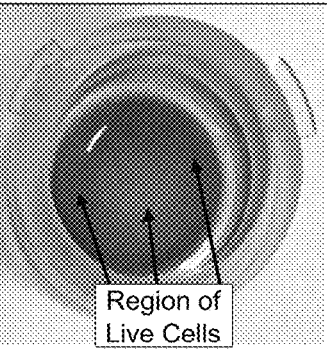<br>Region of Live Cells |

| 4E. | Without L-Ascorbic Acid | With L-Ascorbic Acid |
|---|---|---|
| n-Octanol<br>CASRN 111-87-5<br>Irritant<br>(GHS Classification Category 2) | 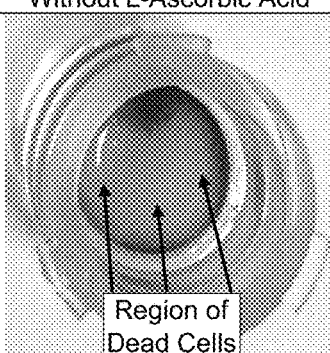<br>Region of Dead Cells | 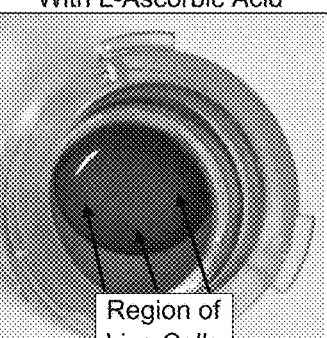<br>Region of Live Cells |

| 4F. | Without L-Ascorbic Acid | With L-Ascorbic Acid |
|---|---|---|
| n,n-Diethyl-m-toluamide<br>CASRN 134-62-3<br>Irritant<br>(GHS Classification Category 2) | 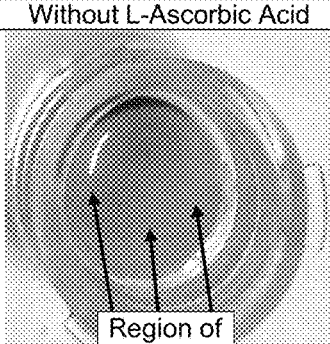<br>Region of Dead Cells | 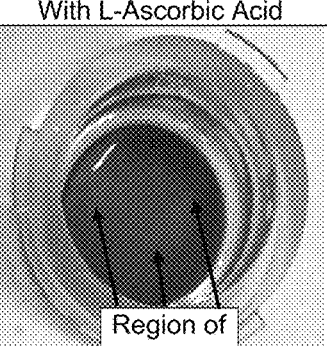<br>Region of Live Cells |

FIGS. 4D-4F

FORMULATIONS AND METHODS RELATED TO EYE IRRITATION

BACKGROUND

Most chemical safety testing for the eye has traditionally been performed using the method of Draize (Draize et al., 1944), as modified by Kay and Calandra (Kay and Calandra, 1962). This now-controversial procedure involves instilling the substance under evaluation within the conjunctival sac of a New Zealand White rabbit. Indices of toxicity are recorded for the cornea, iris, and conjunctiva at regular time intervals for up to 21 days.

Draize test data have traditionally been used to derive a numerical score of ocular irritation; however, modern classification systems use the same data with a slightly different statistical treatment to develop an irritation category. Modern ocular irritation classification schemes include the European Union (EU), Globally Harmonized System of classification and labeling of chemicals (GHS), and Environmental Protection Agency (EPA) systems, which are not harmonized with one another. The EU Dangerous Substance Directive (DSD) classification and labeling system does not include cosmetics; it was applied in accordance with the Commission Directive 2001/59/EC and includes categories R41 (risk of serious damage to the eye) and R36 (ocular irritant) (EC, 2001). DSD was replaced by the Classification, Labeling, and Packaging (CLP) regulation aligned with GHS (EC, 2008a). The GHS system includes classes NC (not classified as an irritant), 2A (reversal by 7 days), 2B (reversal by 14 days), and 1 (no reversal by 21 days) (EC, 2008b; UN, 2011). GHS classification is used to satisfy U.S. Food and Drug Administration and international safety labeling requirements and plays an important role in commercial product liability and consumer product satisfaction. Guidance documents produced by the Organization for Economic Trade and Development (OECD) are available to coordinate international trade. The OECD describes the standard rabbit eye test (the gold standard for GHS eye safety classification), which is required for safety data sheet documentation accompanying hazardous chemicals and products.

The EPA classification includes classes I (corrosive), II (moderate irritant), III (mild irritant), and IV (nonirritant), in accordance with the guidelines in the Label Review Manual (US EPA, 2003) and based on test methods described in the Acute Eye Irritation Health Effects Test Guideline (US EPA, 1998). Corrosives result in irreversible damage to the eye, whereas ocular irritation is reversible. EPA class III includes irritation at 24 h. The GHS classification system, now widely accepted in the EU, does not include a category with a comparable short-duration sensitivity limitation. The EPA classification system is required for agrochemicals and other registrations and has commercial significance, especially for cosmetics and personal care products used around the eye.

One of the needs for nonanimal safety tests originated from bans or pending bans on the use of animals for the safety of cosmetics and other products. The EU banned animal testing of finished cosmetic products in 2004, animal-tested ingredients 4 years later, and the transport and sale of cosmetics containing ingredients tested on animals in 2013, pledging to push other parts of the world to accept alternatives (Kanter, 2017). As of 2014, there are bans or severe limitations in Norway, Israel, India, and Brazil (Senate Joint Resolution 22, 2014), and by 2017, the list of countries had grown to 37, according to the Humane Society of the U.S. (Humane Society, 2017).

The United States has been slow to ban animal testing or mandate the use of nonanimal alternatives in the product testing industry; however, recent legislation will ban animals for a wide range of testing applications that have traditionally used live animals. Bill H.R.2790 "The Humane Cosmetics Act" was introduced on Jun. 6, 2017 and would prohibit animal testing of cosmetics within 1 year and the sale or transport of cosmetics tested on animals within 3 years after enactment, which is now supported by more than 200 cosmetics companies and stakeholders (H.R.4148, 2014). Additionally, the "Frank R. Lautenberg Chemical Safety for the 21st Century Act"—S.697, which revises the Toxic Substances Control Act of 1976 (TSCA)—was passed on Jun. 22, 2016. The TSCA now requires EPA to evaluate existing and new chemicals to determine whether regulatory control of a certain chemical is warranted and if it presents an unreasonable risk of injury to health or the environment so as to reduce risks to a reasonable level. The law also requires EPA to "reduce and replace, to the extent practical . . . the use of vertebrate animals in testing chemicals to provide information of equivalent or better scientific quality and relevance for assessing risks of injury to health or the environment of chemical substances or mixtures . . . " and to develop a strategic plan within 2 years of enactment or by June 2018 (S.697, 2016). Section 4 of the new law includes specific guidance on the use of nonanimal tests when available for initial screening and tiered testing of chemical substances and mixtures (S.697, 2016). Therefore, an accurate and internationally accepted nonanimal test for ocular irritation is needed.

In light of these issues, increased interest has focused on the development of nonanimal testing methods and strategies to replace the Draize live animal eye irritation test. Toward this end, the Interagency Coordinating Committee for the Validation of Alternative Methods (ICCVAM) and the European Centre for Validation of Alternative Methods (ECVAM) conducted retrospective evaluations of data available for four organotypic methods and four cytotoxicity and cell function test methods. Based on these retrospective evaluations, the predictive performance of all individual test methods was not felt to be sufficient for any one test, or group of tests, to fully replace the rabbit Draize eye test (ICCVAM, 2009). ICCVAM and ECVAM did, however, accept the bovine cornea opacity and permeability ("BCOP") test, isolated chicken eye test, cytosensor microphysiometer (CM, for water-soluble materials), and fluorescein leakage test (for water-soluble materials) as screening tests for the identification of materials classified as NC, ocular corrosives, and severe eye irritants, and the CM as a screening test for the identification of materials classified as NC (surfactants and surfactant mixtures). Recently, differentiated cell culture models, including the EPIOCULAR eye irritation test, the SKINETHIC human corneal epithelium, and the LABCYTE CORNEA-MODEL24, were demonstrated to have utility for the detection of NC (OECD, 2019a).

No single nonanimal test, or combination of nonanimal tests, can currently detect GHS-classified reversible irritation with any degree of statistical certainty (Wilson et al., 2015).

Overall, there are a limited number of types of ocular irritation tests that do not require the use of animals. These tests include cell culture-based tests, tests based on excised animal eyes, egg-based tests, and biochemical tests. All of these tests fail to identify or model some essential component of the live eye and have either poor specificity or sensitivity. The lack of understanding of the underlying reasons why some substances are much more damaging than others has hindered the development of nonanimal tests for eye safety testing. All sensitive tests for ocular irritation have a high false-positive rate (about 40%). Those familiar with the state of the art say the high false positive rates of nonanimal tests is because nonanimal tests are only able to measure initial damage, but do not accurately model the repair/reversibility of the damage.

False negatives are dangerous because the nonanimal test predicts that a chemical or product is safe for the eye, when in fact, the substance irritates or corrodes the live eye. False positives are dangerous because people do not believe test methods with a high false positive rate resulting in ignoring warning labels, and manufacturers are slow to adopt methods with a high false positive rate because they erroneously restrict the use of safe products and scare away consumers.

SUMMARY

An in vitro method for predicting ocular irritancy of a test substance is disclosed. The method includes applying the test substance to an in vitro irritancy test system in the presence of an antioxidant formulation under conditions in which antioxidant is allowed to interact with the test substance, including where the antioxidant formulation is: (1) mixed with the test substance prior to applying to the test system, (2) added to the test system prior to applying the test substance, (3) or both (1) and (2); measuring a test system response; and predicting the ocular irritancy of the test substance based on the test system response.

In some embodiments of the method, the antioxidant formulation comprises one or more compounds selected from ascorbic acid, baicalein, beta-carotene, bilirubin, caeruloplasmin, catechin, cobalamin, coenzyme Q10, cortisone, cryptoxanthin, crystallin, curcumin, cyanidin, delphinidin, epigallocatechin-3-gallate, esculetin, estradiol, estriol, folic acid, genistein, glutathione, glutathione peroxidase, human serum albumin, idebenone, kaempferol, L-acetylcarnitine, L-cysteine, lipoic acid, L-tyrosine, lutein, lycopene, melatonin, mexidol, myo-inositol, myricetin, N-acetyl cysteine, estrogen, omega-3, omega-6, omega-9, pelargonidin, peonidin, petunidin, piceatannol, pigment epithelium derived factor, quercetin, resveratrol, riboflavin, selenium, silymarin, superoxide dismutase, taurine, tempol, thiamine, thioredoxin, thymoquinone, transferrin, ubiquinol-10, uric acid, vitamin A, vitamin D3, vitamin E, and zeaxanthin.

In some embodiments, the antioxidant formulation comprises about 0.27-60 mM ascorbic acid.

In some embodiments, the test system is a biochemical test system comprising purified or semi-purified molecules. In other embodiments, the test system comprises reconstituted human corneal epithelium (RhCE). In other embodiments, the test system is a Depth of Injury (DoI) test system comprising excised eyes.

In one embodiment, the test system is selected from the OPTISAFE ocular irritation test, the IRRITECTION ocular irritation test, the EPIOCULAR ocular irritation test, the SKINETHIC ocular irritation test, the LABCYTE CORNEA-MODEL24 ocular irritation test, the MCTT HCE™ ocular irritation test, the Short Time Exposure ocular irritation test, the HET-CAM ocular irritation test, the CAMVA ocular irritation test and the DEPTH OF INJURY (DoI) ocular irritation test.

A method for reducing false positive rates of nonanimal eye irritation tests is disclosed. The method includes: overlaying an antioxidant formulation onto a surface of a differentiated eye tissue, comprising reconstituted human corneal epithelium or excised eye tissue; adding a test substance to the antioxidant formulation on the surface of the differentiated eye tissue; exposing the differentiated eye tissue to the test substance for a first period of time; washing the surface of the differentiated eye tissue with a buffered salt solution to remove the test substance; after a second period of time, measuring cell viability of the differentiated eye tissue; and relating the measured cell viability to an index of irritation, which can be categorized according to established ocular irritancy classes, where the false positive rate is reduced compared to performing the method without overlaying with the antioxidant formulation.

In some embodiments of the method for reducing false positive rates, the established ocular irritancy classes are selected from a nonirritant, a minimal irritant, a mild irritant, and a severe irritant. In other embodiments, the established ocular irritancy classes include GHS categories NC, 2, 2B, 2A, and 1, or EPA categories IV, III, II, and I.

In some embodiments, the antioxidant formulation comprises 1.70 mM (0.3 mg/ml) L-ascorbic acid, 1% bovine serum albumin and 5% dextran in a buffered saline solution, adjusted to a pH of 7.35.

In some embodiments, the washing step further comprises a subsequent wash with additional antioxidant formulation.

An antioxidant formulation is disclosed. The formulation includes L-ascorbic acid at a concentration of about 0.27-60 mM, serum albumin at a concentration of about 0.05% to 10%, and dextran at a concentration of about 3% to 30%, in a buffered saline solution, where the formulation has a pH of between 7-7.5.

In one embodiment, the L-ascorbic acid has a concentration of about 1.70 mM (0.3 mg/ml).

In one embodiment, the serum albumin is bovine serum albumin at a concentration of 1%.

In one embodiment, the dextran has a concentration of 5%.

In one embodiment, the buffered saline solution includes about 6 mg/ml NaCl in a HEPES buffer In some embodiments, the formulation reduces the false positive rate of in vitro nonanimal eye irritation tests.

In some embodiments, the formulation reduces the damage caused by exposure to eye irritants in vivo. In a particular embodiment, the post-exposure protective formulation includes L-ascorbic acid at a concentration of 17.0 mM (3 mg/ml).

A procedure and reagent are disclosed for the accurate prediction of eye toxicity after a chemical, product, or material exposure in which antioxidants that model those found in the live eye are added, and the addition of the antioxidants results in a lower FP rate, as determined by comparing the nonanimal test method FP rate to the live animal or human TN rate.

In some embodiments, known irritants may include one of more of the following: dodecanaminium, N-(2-hydroxy-3-sulfopropyl)-N,N-dimethyl-,1-naphthaleneacetic acid, 1-octanol, 1,2,4-triazole, sodium salt, 1,3-di-isopropylbenzene, 1,3-diiminobenz (f)-isoindoline, 1,5-hexadiene, 2-benzyl-4-chlorophenol, 2-benzyloxyethanol, 2-ethoxyethyl acetate (cellosolve acetate), 2-ethyl-1-hexanol, 2-hydroxyisobutyric acid ethylester, 2-hydroxyisobutyric acid, 2-methyl-1-pentanol, 2-methylbutyric acid, 2-naphthalene sulfonic acid, formaldehyde, hydroxymethylbenzene sulfonic acid monosodium salt, 2-nitro-4-thiocyanoaniline, 2,2-dimethyl-3-pentanol, 2,2-dimethyl butanoic acid, 2,5-dimethyl-2,5-hexanediol, 2,6-dichlorobenzoyl chloride, 2,6-dichloro-5-fluoro-beta-oxo-3-pyridinepropanoate, 3-chloropropionitrile, 3,3-dithiodipropionic acid, 3,4-dichlorophenyl isocyanate, 4-(1,1,3,3-tetramethylbutyl)phenol, 4-tert-butylcatechol, 4-carboxybenzaldehyde, 4-chloromethanilic acid, 6-methyl purine, p-tert-butylphenol, acetic acid, acetone, acid blue 40, acid red 92, alpha-ketoglutaric acid alpha, ammonia, aluminum chloride, gamma-aminopropyltriethoxy silane, ammonium nitrate, antimony oxide, benzalkonium chloride, benzalkonium chloride (10%), benzenesulfonyl chloride, benzethonium chloride (10%), benzene, 1,1'-oxybis-, tetrapropylene derivatives, sulfonated, sodium salts, benzotrichloride, benzyl alcohol, beta-resorcylic acid, bis-(3-aminopropyl) tetramethyl disiloxane, butanol, butyl acetate, butyl cellosolve, butyl dipropasol solvent, butylnaphthalene sulfonic acid sodium salt, butyrolactone, calcium thioglycolate, captan 90-concentrate (solid), camphene, cetylpyridinium bromide (10%), cetylpyridinium chloride (10%), cetyltrimethylammonium bromide (10%), chlorhexidine, chloroform, cyclohexanol, cyclohexanone, cyclohexyl isocyanate, cyclopentanol, deoxycholic acid sodium salt (10%), di(2-ethylhexyl) sodium sulfosuccinate (10%), di(propylene glycol) propyl ether, dibenzoyl-L-tartaric acid, dibenzyl phosphate, diethylaminopropionitrile, domiphen bromide (10%), ethanol, ethyl 2-methyl acetoacetate, ethyl trimethyl acetate, glycidyl methacrylate, granuform, hydroxyethyl acrylate, imidazole, isobutanal, isobutyl alcohol, isopropyl alcohol, lactic acid, lauric acid, lauryldimethylamine oxide, lime, m-phenylene diamine, magnesium hydroxide, maneb, methoxyethyl acrylate, methyl acetate, methyl cyanoacetate, methyl cyclopentane, methyl ethyl ketone (2-butanone), methyl isobutyl ketone, methylpentynol, methylthioglycolate, myristyl alcohol, n-acetylmethionine, n-butanol, n-hexanol, n-laurylsarcosine sodium salt (10%), n-octylamine, N,N,N',N'-tetramethylhexanediamine, naphthalenesulfonic acid, 2-naphthalenesulfonic acid, sodium salt, nitric acid, organofunctional silane 45-49, phosphorodicloridic acid, hydrogenated tallow amine, polyoxyethylene(23) lauryl ether, potassium laurate (10%), potassium oleate, promethazine hydrochloride, potassium hydroxide, protectol PP, pyridine, benzyl-C12-16-alkyldimethyl, silver nitrate, sodium 2-naphthalenesulfonate, sodium hydrogen difluoride, sodium hydrogen sulfate, sodium hydroxide (10%), sodium lauryl sulfate, sodium lauryl sulfate (15%), sodium monochloroacetate, sodium oxalate, sodium perborate tetrahydrate, sodium polyoxyethylene(3) lauryl ether sulfate, sodium salicylate, stearyltrimethylammonium chloride, sulfuric acid, tetra-N-octylammonium bromide, tetraethylene glycol diacrylate, tetrahydrofuran, trichloroacetic acid (30%), trichloroacetyl chloride, triethanolamine, triethanolamine polyoxyethylene(3.0) lauryl ether sulfate, triton X-100, triton X-100 (5%), triton X-100 (10%).

In some embodiments, known nonirritants may include one or more of the following: 1-bromo-4-chlorobutane, styrene, 1,9-decadiene, 2-ethylhexyl p-dimethylamino benzoate, 2-methylpentane, 2-(n-dodecylthio)-ethanol, 2,2-dimethyl-3-pentanol, 2,4-difluoronitrobenzene, 2,4-pentanediol, 3-methoxy-1,2-propanediol, 3-methylhexane, 3,3-dimethylpentane, acrylic acid homopolymer sodium salt, di-n-propyl disulphide, diisobutyl ketone, ethylhexyl salicylate, glycerol, iso-octyl acrylate, isopropyl bromide, isopropyl myristate, iso-octylthioglycolate, methyl trimethyl acetate, n-hexyl bromide, n-octyl bromide, n,n-dimethylguanidine sulfate, polyethylene glycol 400, polyethyleneglycol monolaurate (10 E.O.), polyoxyethylene hydrogenated castor oil (60E.O.), polyoxyethylene(14) tribenzylated phenyl ether, polyoxyethylene(160) sorbitan triisostearate, polyoxyethylene (40) hydrogenated castor oil, potassium tetrafluoroborate, propylene glycol, sodium lauryl sulfate (3%), sorbitan monolaurate, tetra-aminopyrimidine sulfate, toluene, triton X-100 (1%), and tween 80.

In some embodiments, antioxidants may include one of more of the following: apigenin, ascorbic acid (about 0.27-60 mM), baicalein, beta-carotene: 0.5-50 μM, bilirubin, caeruloplasmin, catalase (0.6-60 μM), catechin, cobalamin, coenzyme Q10, cortisone, cryptoxanthin, crystallin, curcumin, cyanidin (0.01-50 μM), delphinidin (0.01-50 μM), epigallocatechin-3-gallate, esculetin, estradiol, estriol, folic acid, genistein, glutathione (1.0-107 μM), glutathione peroxidase, human serum albumin, idebenone, kaempferol, L-acetylcarnitine, lipoic acid, L-tyrosine (0.5-45 μM), lutein (0.5-50 μM), lycopene, melatonin, mexidol, myo-inositol, myrecitin, N-acetyl cysteine, estrogen, omega-3, omega-6, omega-9, pelargonidin (0.01-50 μM), peonidin (0.01-50 μM), petunidin (0.01-50 μM), piceatannol, pigment epithelium derived factor (0.8-80 μM, quercetin, resveratrol, riboflavin, selenium (0.2-20 μM), silymarin, superoxide dismutase (1.0-100 μM), taurine (0.2-22.6 μM), tempol, thiamine, thioredoxin, thymoquinone, transferrin (0.08-80 μM), ubiquinol-10, uric acid (0.4-43 μM), vitamin A (1.7-172.7 μg/mL), vitamin D3, vitamin E (0.5-50 μM), and zeaxanthin (0.5-50 μM).

As used herein, "toxicity" is used to refer to a substance's ability to damage, irritate, or otherwise negatively affect an eye. Toxicity may be evidenced by pain, irritation, swelling, opaqueness, redness, and discharge. Such effects may be temporary or permanent. Accordingly, the word "toxicity" is defined broadly to include any discomfort or unfavorable experience associated with the presence of a substance contacting an eye. As used herein, "irrancy" or "irritant" is used broadly to cover the spectrum of between nonirritating (nontoxic) to highly corrosive.

BRIEF DESCRIPTION OF THE DRAWINGS

FIGS. 4A-4F depict results from the modified EPIOCULAR reconstituted human corneal epithelium test system in which a high concentration (17 mM ascorbic acid) antioxidant formulation was added. Nonirritants=FIG. 4A. n-Hexyl bromide CASRN 111-25-1, FIG. 4B. Dioctyl ether CASRN 629-82-3, and FIG. 4C. Isopropyl myristae CASRN 110-27-0. Irritants=FIG. 4D. Methyl acetate CASRN 79-20-9, FIG. 4E. n-Octanol CASRN 111-87-5, and FIG. 4F. n,n-Diethyl-m-toluamide CASRN 134-62-3.

DETAILED DESCRIPTION

Figures 1A, 1B:
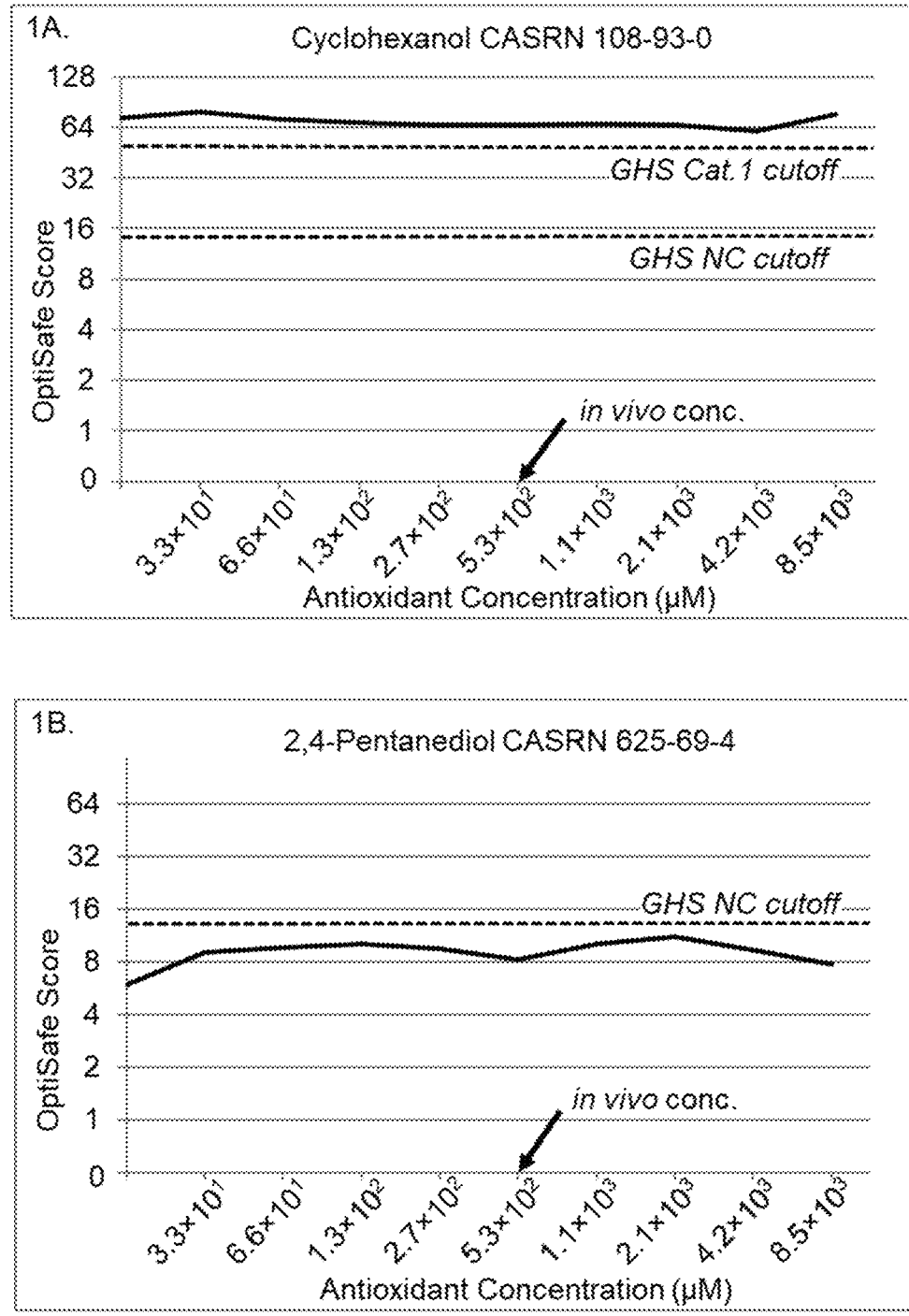
FIGS. 1A-1G depict control antioxidant titrations. Positive control=FIG. 1A. Cyclohexanol CASRN 108-93-0. Negative controls=FIG. 1B. 2,4-Pentanediol CASRN 625-69-4 and FIG. 1C. Dodecane CASRN 112-40-3. False-positive controls=FIG. 1D. Triphenyl phosphite CASRN 101-02-0, FIG. 1E. Ethyl acetate CASRN 141-78-6, FIG. 1F. 2,4-Pentanedione CASRN 123-54-6, and FIG. 1G. 2,2-Dimethyl-3-pentanol CASRN 3970-62-5. The dashed line shows the GHS NC cut-off.
Figure 1C:
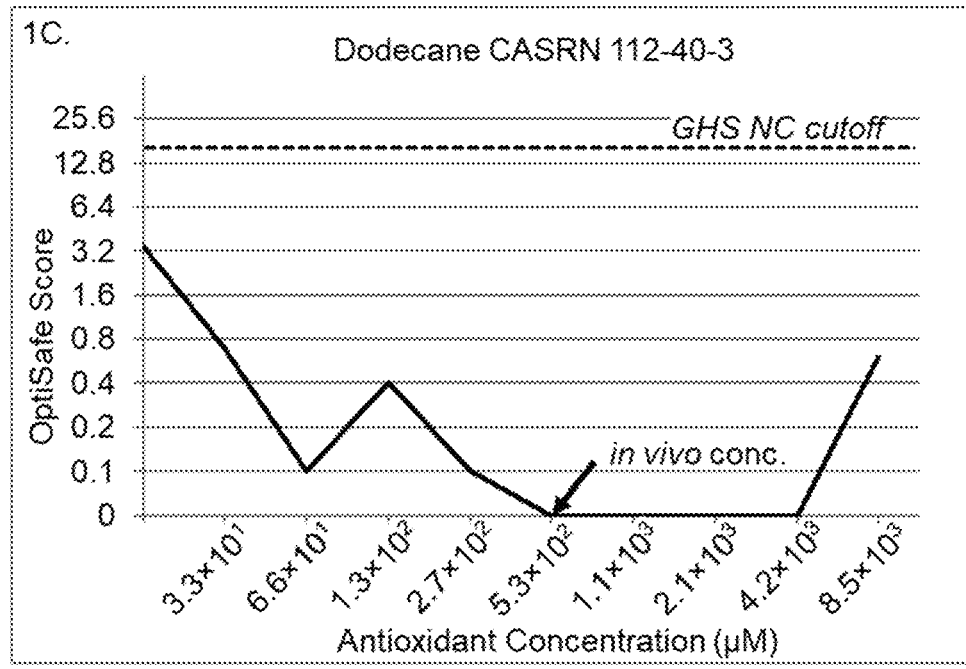
Figure 1D:
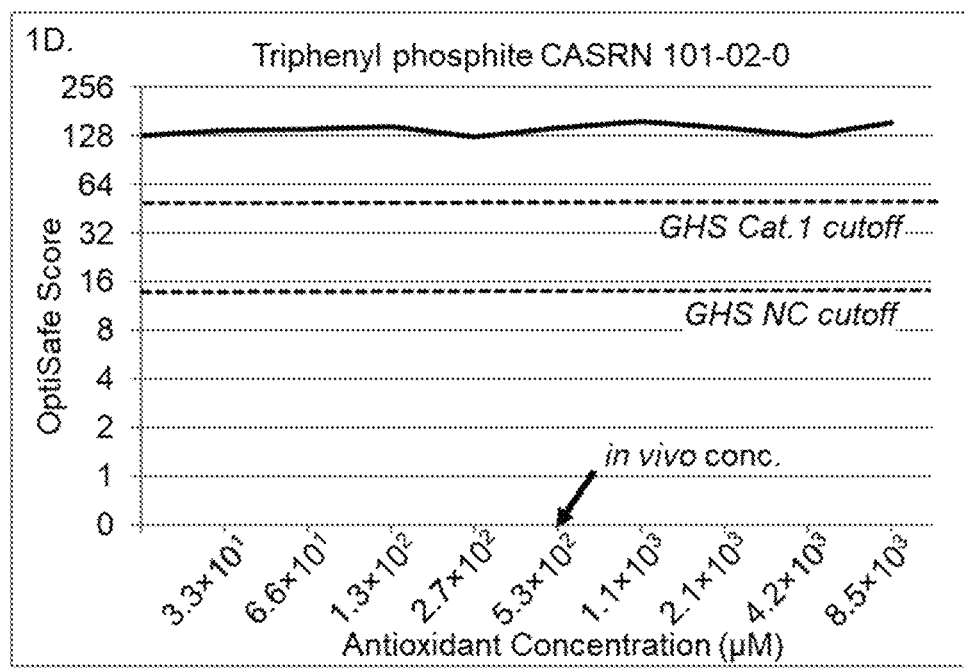
Figure 1E:
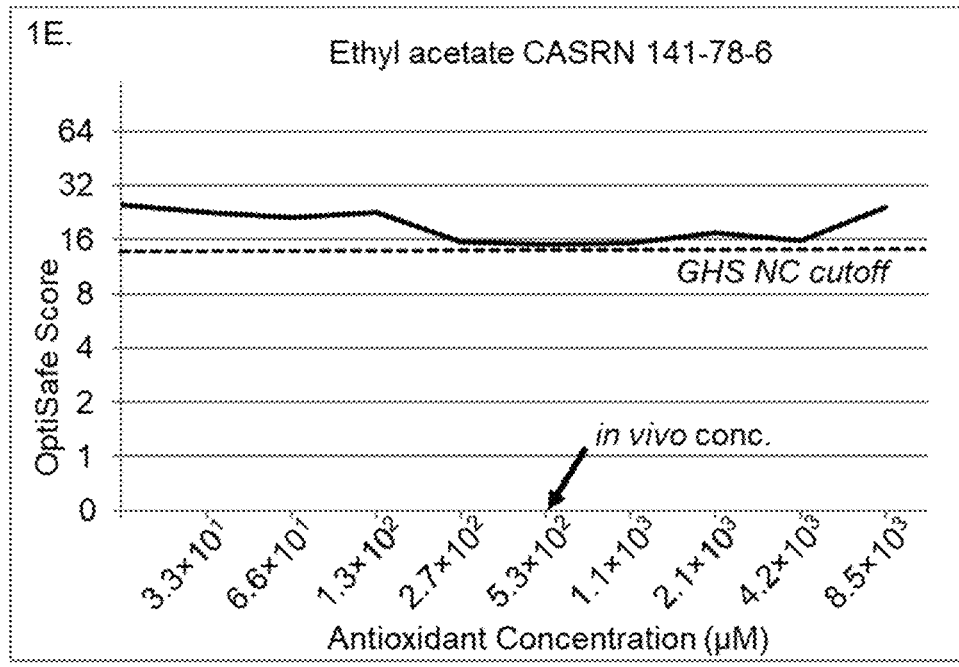
Figure 1F:
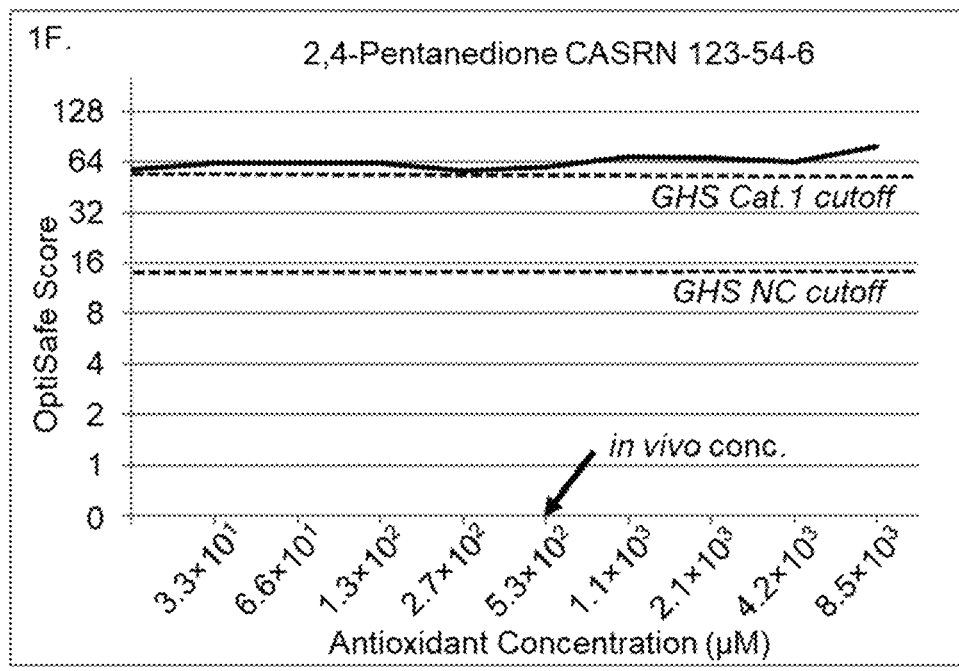
Figure 1G:
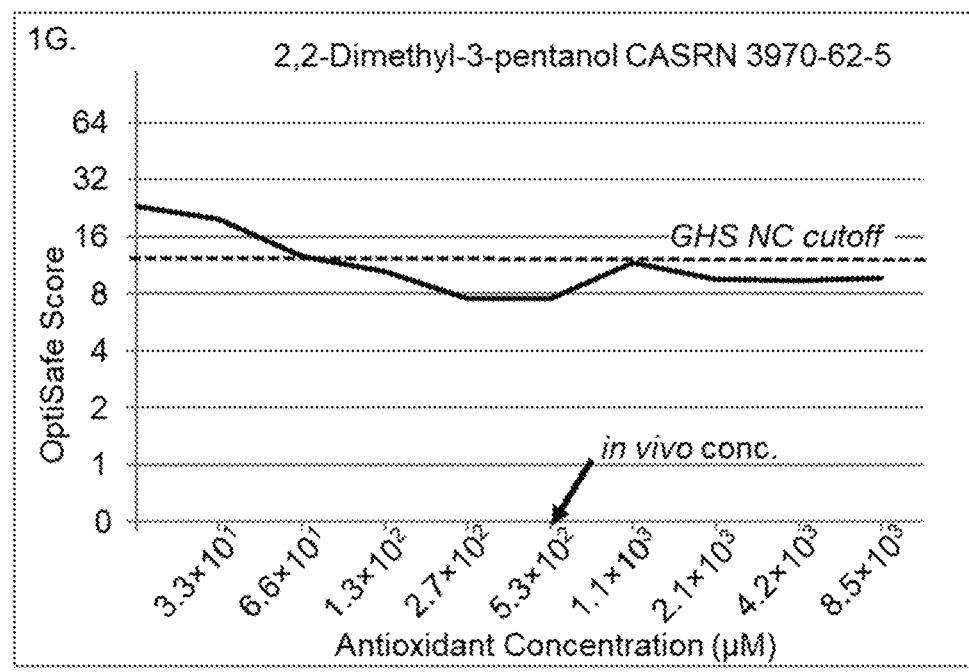
Figure 2A:
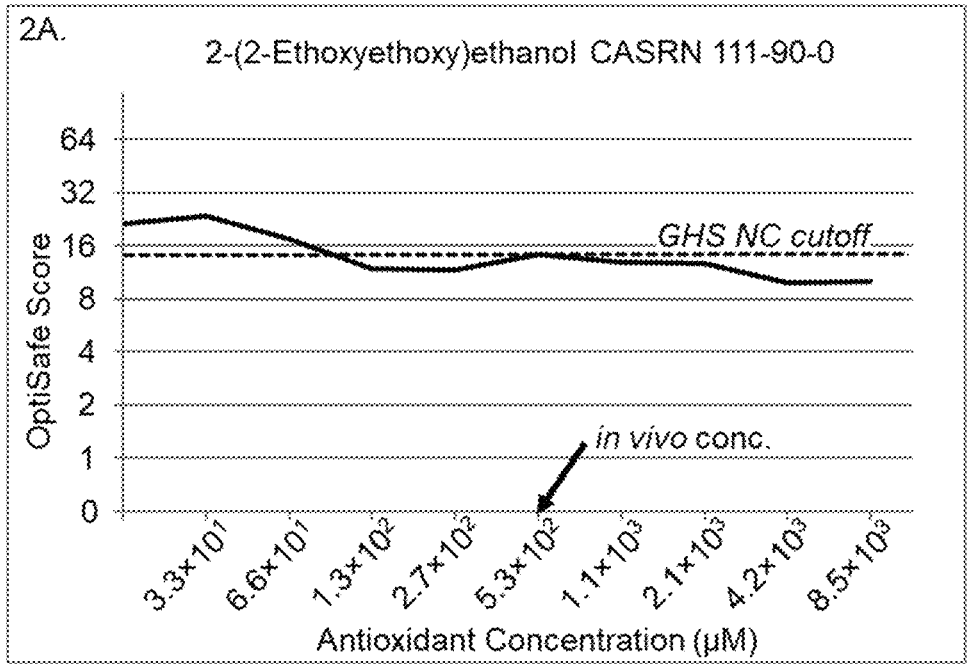
FIGS. 2A-2F depict reactive oxygen species (ROS) and crosslinker (CL) antioxidant titrations. ROS chemicals (previously classified as false positives)=FIG. 2A. [2-(2-Ethoxyethoxy) ethanol CASRN 111-90-0, FIG. 2B. Triethylene glycol CASRN 112-27-6, FIG. 2C. Ethylene glycol diethyl ether CASRN 629-14-1, and FIG. 2D. Styrene CASRN 100-42-5. Cross-linkers (previously predicted as false positives)=FIG. 2E. (1,9-Decadiene CASRN 1647-16-1 and FIG. 2F. 2-Ethoxyethyl methacrylate CASRN 2370-63-0). The dashed line shows the GHS NC cut-off.
Figure 2B:
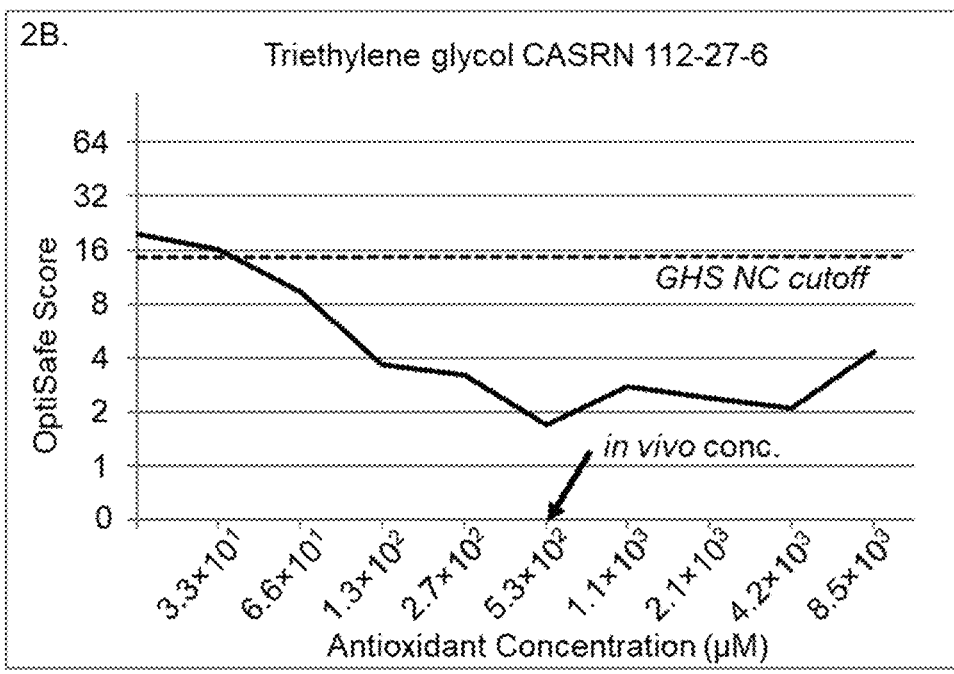
Figure 2C:
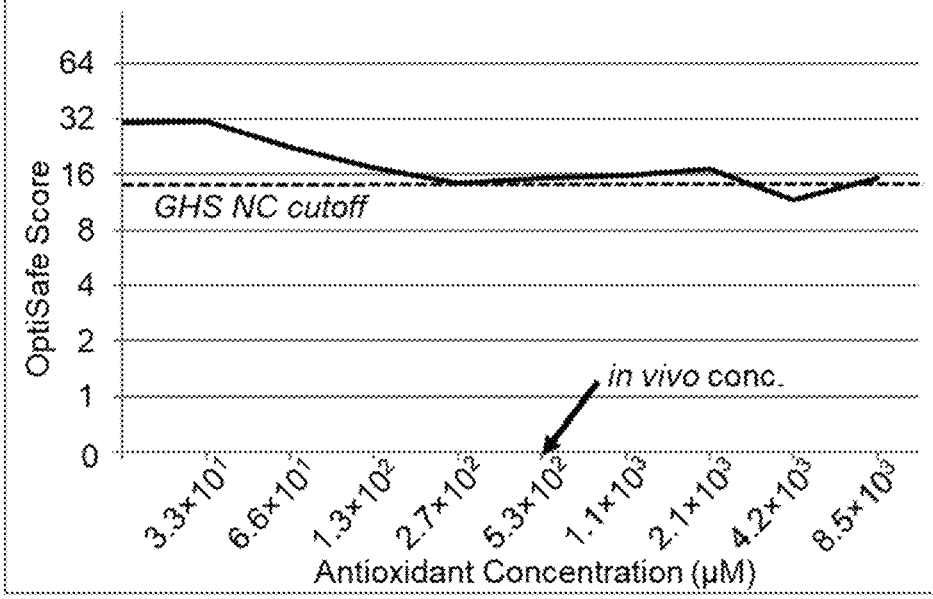
Figure 2D:
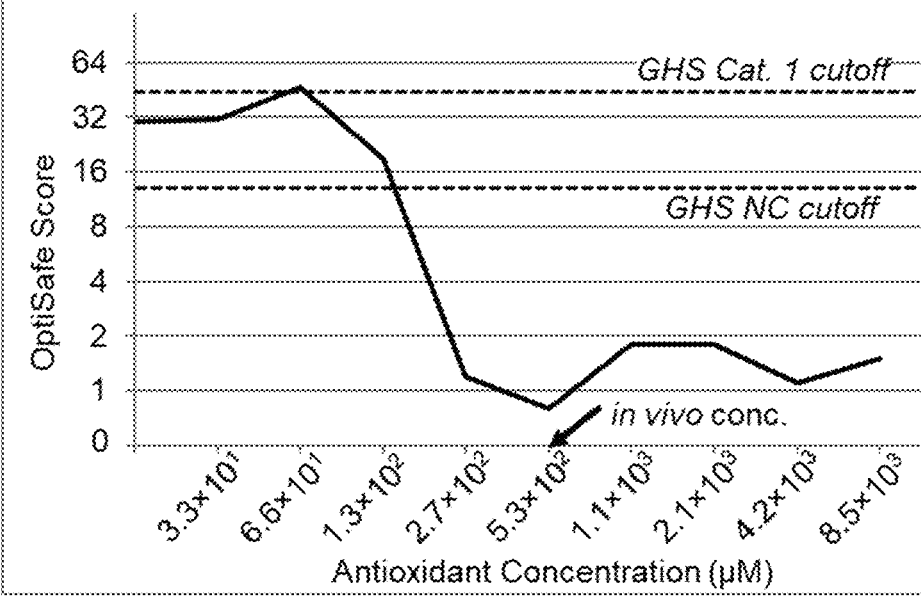
Figure 2E:
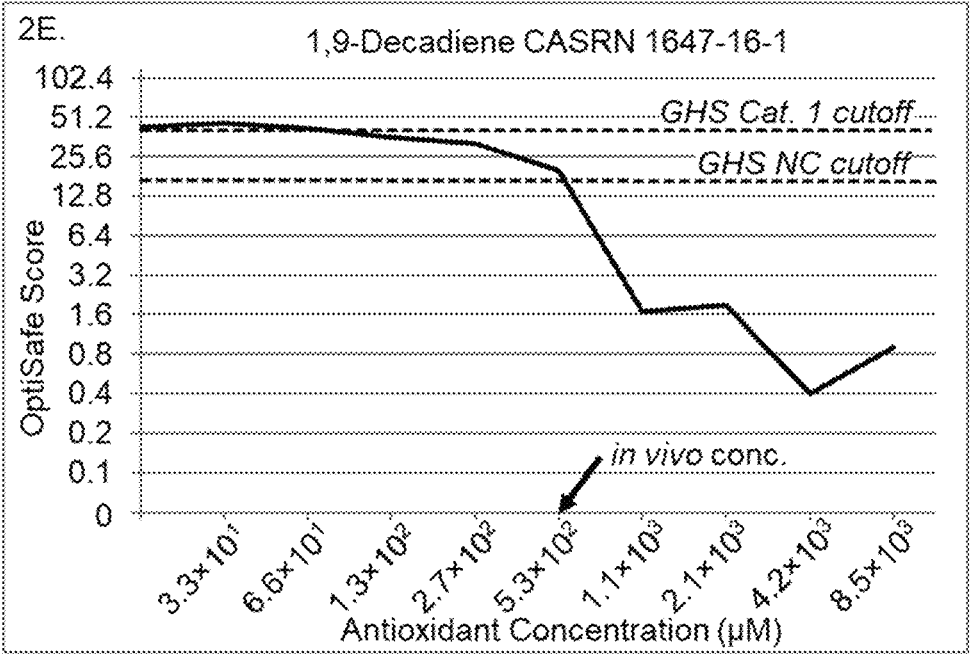
Figure 2F:
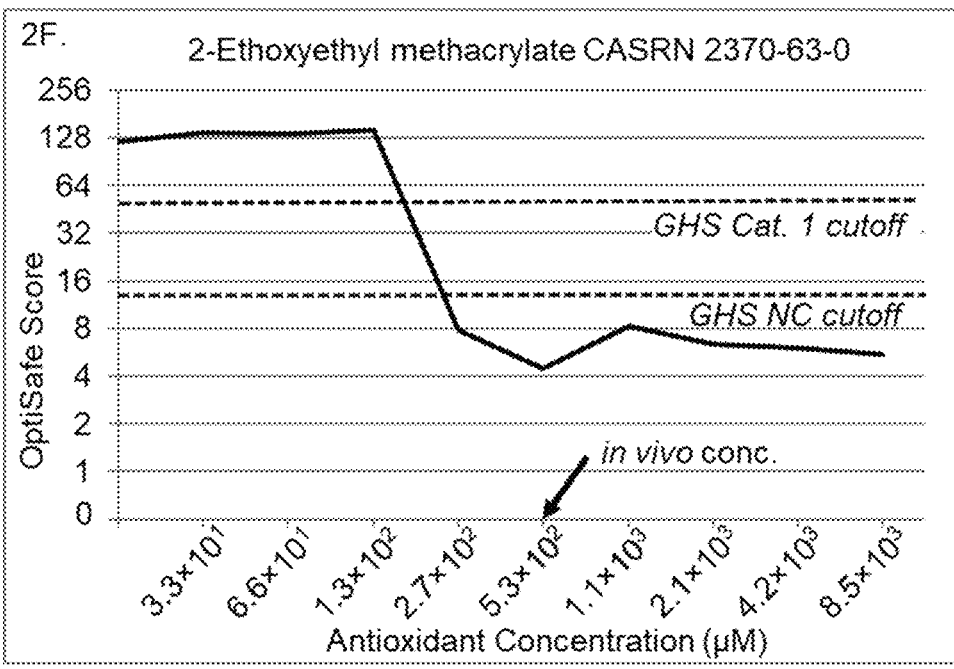

As disclosed herein, the inventors have discovered that high false positive rates exhibited by current nonanimal ocular irritancy tests can be substantially reduced and/or prevented by adding antioxidants, in particular those found in tears, to in vitro test systems. The high false positive rates of current nonanimal tests are likely not only because of a failure to reverse damage caused by irritants after it has occurred, but also by a failure of nonanimal tests to model other aspects of the live eye, including the antioxidant properties of tears, which theoretically prevent initial damage by inactivating reactive molecules before they have a chance to damage ocular tissue. As described below, although nonanimal eye tests have been in development for over 25 years, the prevention of chemical damage by modeling tear related antioxidant activity has not been a consideration for test development or strategy to reduce the false positive rate. Indeed, conventional wisdom has led the skilled artisan away from using antioxidants in nonanimal test systems, because these tests have been purposely biased to maximize sensitivity, such that the reduction of measured damage by inactivating reactive molecules has been viewed as reducing the sensitivity of the test method. Nonetheless, as disclosed herein, the addition of live eye related antioxidants specifically and substantially reduced the false positive rate, without reducing sensitivity (i.e., no increase in false negatives). Consequently, the specific and substantial reduction in false positive rate is an important and unexpected finding.

Cell culture-based tests typically involve applying the test substance to epithelial tissues grown in a dish to determine its toxicity based on the degree of cells killed by the substance after a fixed time. These tests only examine the outermost layer of the eye (the epithelium). These cells are either skin cells or genetically modified cells that do not contain the antioxidants or chemical composition of tears or the corneal stroma. As shown in Table 1 below, common cell culture media either does not include antioxidants, or as in the case of MEM medium used for the BCOP test, contains a concentration of antioxidant (ascorbic acid) far lower than that found in tears. Further, as detailed below, antioxidant is not added to the test substance or included during the time the test substance is exposed to the cultures.

TABLE 1

Media Used for Cell Culture, Differentiated Tissue and Organ Culture Tests

| Media | Ascorbic Acid (Y/N) | Media Concentration | Aqueous Humor[1,2] | Tear[3] |
|---|---|---|---|---|
| EMEM ATCC 30-2003 (short time exposure; STE Test MEDIA) | N | none | 0.81 mM | 1.3 mM |
| DMEM High Glucose [+] Pyruvate [+] Phenol Red Cat# 11995 (used for tissue and cell culture tests) | N | none | 0.81 mM | 1.3 mM |
| MEM Alpha [+] Nucleosides [−] Phenol Red (USED FOR BCOP) | Y | 0.17 mM | 0.81 mM | 1.3 mM |
| DMEM 2902 Low glucose [−] phenol red (used for tissue and cell culture tests) | N | none | 0.81 mM | 1.3 mM |

[1]de Berardinis et al., 1965.
[2]https://emedicine.medscape.com/article/2088649-overview
[3]Paterson and O'Rourke, 1987.

Tests based on fertilized eggs, or the HET-CAM, measure changes to the vessels that extend from the developing yolk to the air cell within the egg; this primitive respiratory tissue (CAM) is a system that is very different from the eye, does not measure antioxidant effects on the eye, and is a visual test that does not detect transparency changes. No antioxidants are added to this test system.

Organotypic tests using cow, chicken, rabbit, human or pig eyes measure changes in opacity and permeability (e.g., BCOP test) or fluorescein retention and/or cornea thickness (e.g., ICE test, PORCORA etc), depth of injury and viability (DoI test and other organotypic tests). Excised eyes may or may not be metabolically active and may contain some residual antioxidant activity within the tissue. However, any such residual antioxidant activity is much lower than that found in tears, and no tear-like supplement or antioxidant is added at the same time as the test substance to mimic the tearing process and process of tear and antioxidant mixing with the test substance prior to interacting with tissues.

In addition, these tests use typically use an off the shelf tissue culture medium that may include some low level of antioxidant (below the levels found in tears as explained above), however, these tissues are fed from the bottom (endothelial side) and the test chemical is applied to the outermost region of the eye (epithelial side). Therefore, the low levels of antioxidants in the medium are in the wrong location to interact with the chemical when it is applied to the epithelial side, and the reaction kinetics of reactive oxygen species tissue damage are extremely fast, to be effective, the antioxidant mix must form a layer between the tissue and the chemical, as in tear film. Therefore, low levels of antioxidants in tissue culture medium do not reduce the false positive rates of these tests. These tests exhibit high false-positive (FP) rates that do not accurately approximate the live animal response to the same chemicals indicating they are missing a variable required to control the false positive rate.

Although the nonanimal alternative eye toxicity tests described above have been performed for many years, toxicologists and those skilled in the art do not know all of the underlying reasons why some substances cause persistent or permanent damage to the live eye, while damage caused by other substances is repaired quickly; and why the available nonanimal tests all appear to overpredict the toxicity in several classes of chemicals (and up until now, these classes, including oxidants, have not been recognized) compared to live animal or human eye test results. Nonetheless, modern toxicity classification for labeling and safety data sheets, as well as for other uses, depends on the time until recovery to classify a substance as toxic or nontoxic to the eye; predicting whether the live eye can repair or prevent lesions is critical to understanding toxicity and provides a regulatory classification for a chemical or product.

The Unique Redox Environment of the Eye

The cornea consists of a stroma that is protected by a 5-7-layer thick corneal epithelium. This epithelium is stratified, nonkeratinized squamous tissue. The conjunctiva is composed of 3-5 cell layers of stratified, nonkeratinized cells. The cornea and conjunctiva function as barriers to protect the eye from exposure to environmental insults including foreign bodies, microbes, and irritating chemicals.

Tear film consists of three layers—mucin, aqueous, and lipid (inner to outer) that contribute to the health and maintenance of the ocular surface (Conrady et al., 2016). Lacrimal glands produce the aqueous layer of the tear film, which is produced at a basal rate of up to 2 microliter per minute (Kim et al., 2019) and up to 100-fold higher in response to mechanical, thermal, or chemical exposure (reflex rate). These increased aqueous tears dilute, clear, and detoxify chemicals (discussed in detail below).

The human eye contains the mucosal surface of body that is most exposed to the surrounding environment, including atmospheric oxygen, toxic chemicals, and radiation/ROS produced in situ from light-induced oxidative damage. Current nonanimal tests do not include this mucosa, lacrimal gland, or model tears, which is the first biological fluid to interact with chemicals that contact the eye. A significant effect on ocular surface inflammation, corneal epithelium lesions, and ocular discomfort is related to dry eye and increased tear film osmolarity. The tear film has significant levels of antioxidants.

In particular, the cornea is protected against reactive oxygen species (ROS) that include superoxide anion ($O_2$), hydrogen peroxide ($H_2O_2$), hydroxyl radical (HO*), hydroperoxides (ROOH), peroxyl radicals (ROO*), and singlet oxygen ($O_2$) (Nita and Grzybowski, 2016; Ung et al., 2017). Cellular phospholipid bilayers are susceptible to ROS-induced damage via lipid peroxidation, which occurs when free radical species including oxyl radicals, peroxyl radicals, and hydroxyl radicals remove electrons from lipids and subsequently produce reactive intermediates that can cause massive damage via redox cycling (Njie-Mbye et al., 2013; Babizhayev, 2016; Tangvarasittichai, 2018; Su et al., 2019). The oxidation of nucleotides and proteins may lead to changes in gene expression, mutations, and the formation of insoluble protein aggregates.

Importantly, the eye is protected against oxidative stress by antioxidants in the cornea, aqueous humor, and tear film. As shown in Table 2, human tear film and aqueous humor have a similar concentration of antioxidants. Tear film is the first biological fluid to interact with and potentially detoxify chemicals that contact the eye. Nonetheless, nonanimal tests do not model tears or the tearing process. Likewise, the aqueous humor is continuously generated and drained and has a composition similar to tear film (Chen, et al; 2009). Aqueous humor production and turnover is a dynamic process, which like tearing, is not modeled by nonanimal tests. In human tears, ascorbic acid and uric acid account for approximately 50% of the total antioxidant activity, with ascorbic acid being the most abundant. Other small molecules, including reduced glutathione, L-cysteine, and L-tyrosine, make up the rest. Enzymes of the aqueous humor include superoxide dismutase (SOD), which has an activity around 3.5 U/mL (Behndig et al., 1998). In the order of abundance in human aqueous humor, nonenzymatic antioxidants include ascorbic acid (530 µM), L-tyrosine (78 µM), uric acid (43 µM), L-cysteine (14.3 µM), and glutathione (5.5 µM). SOD activity is not believed to contribute significantly to the antioxidant defense mechanisms of the aqueous humor (Chen et al., 2009).

TABLE 2

Antioxidants Present in Aqueous Humor and Tear

| Antioxidant | Aqueous Humor[a] | Tear Film[a] |
| --- | --- | --- |
| L-Tyrosine | 78 µM | 45 µM |
| Uric acid | 43 µM | 328 µM |
| Ascorbic acid | 530 µM | 665 µM |
| L-Cysteine | 14.3 µM | 48 µM |
| Glutathione | 5.5 µM | 107 µM |
| Superoxide dismutase | ~5.1 U/mL[b] | 3.5 U/mL[b] |

[a]Chen et al., 2009
[b]Behndig et al., 1998

Even though scientists in the area of ophthalmology have characterized the importance of protective antioxidant effects on the eye in disease, current in vitro eye tests are theoretically limited in their ability to model the response to oxidative stress. Based on our literature review, current nonanimal eye irritation tests have not specifically accounted for the antioxidant capabilities and properties of the eye; especially the tear response that occurs when chemicals first contact the ocular surface.

Current nonanimal eye irritation tests are highly simplified reductionist models without important factors, such as tear film, innervation, and immune responses, that are normally present in the live eye.

Addition of Antioxidants to OPTISAFE In Vitro Ocular Irritation Test

To address the need for a better and more predictive nonanimal ocular irritation test, we have been developing and improving the chemically based, in vitro ocular irritation test, referred to as OPTISAFE. This test can discriminate nonirritants from irritants/corrosives in fewer than 24 h, with only an hour of hands-on time. Furthermore, multiple test samples can be evaluated simultaneously using standard laboratory techniques and equipment with a shelf life of at least 1 year. Recently, results from a validation study showed that OPTISAFE has a very high sensitivity (100%, the only nonanimal/in vitro test with a zero false negative rate) for nonirritant detection and provides a rapid, high-throughput screening method for nonirritants; however, the FP rate was about 40%, which is similar to other available nonanimal eye safety tests.

Since we have noted that in vitro tests, including OPTISAFE, overpredict many of the same chemicals (Lebrun et al., 2020), we questioned whether these false positives might have common chemical reactions that involve the formation of reactive oxygen species (ROS).

We complied a new list that compared overpredictions for eye irritation and toxicity by all the different nonanimal tests. We noticed that nonanimal tests overpredicted the same chemicals that had similar chemical properties. Interestingly, many of these FPs were associated with a specific class of materials, ether-alkoxides or chemicals associated with oxidative chemistry, which cause oxidative damage and generate ROS. This is quite unexpected because oxidative damage and ROS are primary mechanisms of damage to the eye, so it is not expected that there would be a need to control this mechanism of damage to the eye with antioxidants. However, we noticed that a number of oxidants are in fact nonirritants; they are either not toxic or damage is prevented by the live eye. These chemicals became the target for our formulation improvements and resulted in the discovery described here: the requirement to model the antioxidant capacity of the eye in order to not overpredict the toxicity of safe chemicals.

Previous studies have shown that the eye expresses high levels of antioxidants. The eye is exposed to oxidative stress and has mechanisms to defend against ROS on the ocular surface that includes antioxidants in the cornea, aqueous humor, and tear film. The level of antioxidant intake and plasma levels can have effects on eye disease in humans (Cabrera and Chihuailaf, 2011; Umapathy, et al.; 2013).

Discovery began with the inclusion of various antioxidant mixtures into the formulation of the OPTISAFE nonanimal eye irritation test. The antioxidant mixture contains one or more of the following: Glutathione (GSH) (1-10,000 μM), L-cysteine (0.5-5,000 μM), L-tyrosine (0.5-5,000 μM), ascorbic acid (3.0-1,000 mM), and/or uric acid (3.0-30,000 μM). True-negative (TN) and true-positive (TP) chemicals were tested in parallel to ensure that effects of the antioxidant mixtures did not alter the results of the other varying mechanism measured. During development, octanol CASRN 111-87-5 and 2,4-pentanediol CASRN 625-69-4 were used as TP and TN reference standards. The results indicated that the addition of the antioxidant mixture, at any concentration, did not impact the generated scores of the TP and TN.

Methods

The OPTISAFE method was conducted as previously described (Choksi et al., 2020). Briefly, samples were initially evaluated for solubility, pH, and foaming using a standardized procedure. Based on the outcomes, a decision tree was followed to allow for standardized procedural modifications for substances with the following properties: 1) extreme pH, 2) insolubility, and 3) categorized as a surfactant. The procedure differed for materials with these properties. For substances with an extreme pH, the buffering power was evaluated, and standards were adjusted to match. Insoluble materials were floated instead of placed on membrane discs. Surfactants were diluted. Materials were tested for potential to damage to water-soluble or -insoluble macromolecules. Samples were titrated at five dilutions; after incubation, the resulting OD and pH values were compared with quality controls and a standard curve. In some cases (e.g., the OD exceeds the photometric limit of the spectrophotometer or an inverse dose-response curve), no result could be provided ("Criteria Not Met" abbreviated CNM).

Antioxidant Screening

A screen of the six major abundant antioxidants present in aqueous humor and tear film as listed in Table 2 was performed. In some cases, evaluated materials were added to the OPTISAFE formulation, in other cases the antioxidant can be added to the test matrix or to the test substance, and/or overlayed onto test system prior to dosing the test substance on the test system. In certain embodiments, the first thing the test substance interacts with is preferably the antioxidant. For instance, in the OPTISAFE test, this interaction between test substance and antioxidant occurs in the assay matrix, or optionally, as an overlay. In cell and organotypic eye irritation assays, the test substance can be premixed with antioxidant formulation or the antioxidant formulation can be applied as an overlay over the tissue so the chemical to be tested is first in contact with the antioxidant (like tear film in the eye) and then contacts the tissue. In some cases, the antioxidant can be premixed with the test substance, and also added as an overlay to the test cells or assay matrix. Pilot studies were conducted with a representative TP (cyclohexanol CASRN 108-93-0), TN (2,4-pentanediol 625-69-4), and FP (triethylene glycol 112-27-6) associated with ROS generation. Evaluated antioxidants included L-ascorbic acid (CASRN 50-81-7), L-tyrosine (CASRN 60-18-4), uric acid (CASRN 69-93-2), L-cysteine (CASRN 52-90-4), and glutathione (CASRN 70-18-8).

Formulation Studies

After screening of antioxidants, a final formulation was developed and used to test a broader range of chemicals (Table 3). These included four mispredicted FPs associated with ROS; [2-(2-ethoxyethoxy) ethanol CASRN 11-90-0, triethylene glycol CASRN 112-27-6, ethylene glycol diethyl ether CASRN 629-14-1, and styrene CASRN 100-42-5] and two mispredicted FPs associated with crosslinking activity (1,9-decadiene CASRN 1647-16-1 and 2-ethoxyethyl methacrylate CASRN 2370-63-0). Controls included cyclohexanol CASRN 108-93-0 (positive control), 2,4-pentanediol CASRN 625-69-4, and dodecane CASRN 112-40-3 (negative controls), and chemicals previously classified as FPs that were not identified as generating ROS or having CL chemistries (triphenyl phosphite CASRN 101-02-0, ethyl acetate CASRN 141-78-6,2,4-pentanedione CASRN 123-54-6, and 2,2-dimethyl-3-pentanol CASRN 3970-62-5).

TABLE 3

Literature review of in vitro eye test chemicals including common false positives

| Chemical Name | CASRN | Catalog #[b] | in vivo GHS[a] | OptiSafe | ROS/CL | Description | Reference |
|---|---|---|---|---|---|---|---|
| Cyclohexanol | 108-93-0 | 105899 | 1 | TP | No | No evidence for ROS/CL | Fisher, 2000. Frater, 2009. |
| 2,4-Pentanediol | 625-69-4 | 156019 | NC | TN | No | No evidence for ROS/CL | Tei, 2002. Wang, 2003. |
| Dodecane | 112-40-3 | 297879 | NC | TN | No | No evidence for ROS/CL | Chen, 2019. Huber, 2004. |
| 2-(2-Ethoxyethoxy) ethanol | 111-90-0 | 537616 | NC | FP | ROS | Forms hydrogen peroxide and hydroperoxides | Adedara, 2014. Bodin, 2003. |

TABLE 3-continued

Literature review of in vitro eye test chemicals including common false positives

| Chemical Name | CASRN | Catalog #[b] | in vivo GHS[a] | OptiSafe | ROS/CL | Description | Reference |
|---|---|---|---|---|---|---|---|
| Triethylene glycol | 112-27-6 | 95126 | NC | FP | ROS | Forms hydrogen peroxide and hydroperoxides | Zhu, 2012. Mikulas, 2018. |
| Ethylene glycol diethyl ether | 629-14-1 | 224111 | NC | FP | ROS | Forms hydrogen peroxide and hydroperoxides | Di Tommaso, 2011. Clark, 2001. |
| Styrene | 100-42-5 | S4972 | NC | FP | ROS | Forms styrene oxide | Zhang, 2017. Belvedere, 1981. Carlson, 2006. Niaz, 2017 |
| 1,9-Decadiene | 1647-16-1 | 118303 | NC | FP | CL | Used as a crosslinker to promote polymerization | Palmlof, 2000. Smedberg, 1997. |
| 2-Ethoxyethyl methacrylate | 2370-63-0 | 280666 | NC | FP | CL | Used as a crosslinker to promote polymerization | Chirila, 1991. Garcia, 2002. Faraguna, 2015. |
| Triphenyl phosphite | 101-02-0 | T84654 | NC | FP | No | No evidence for ROS/CL | Schwetlick, 1987, 1995. Kovacs, 1973. Liu, 2019. |
| Ethyl acetate | 141-78-6 | 270989 | NC | FP | No | No evidence for ROS/CL | Suksomtip, 2010. Nakchat, 2014. |
| 2,4-Pentanedione | 123-54-6 | P7754 | NC | FP | No | No evidence for ROS/CL | Mottley, 1991. Rodrigues, 2006. |
| 2,2-Dimethyl-3-pentanol | 3970-62-5 | D173622 | NC | FP | No | No evidence for ROS/CL | Dwarakanath, 1998. Gierke, 1999. Hurley, 2008. |

CASRN = Chemical Abstracts Service Registry Number; GHS = Globally Harmonized System of classification and labelling of chemicals; NC = Not classified; ROS = Reactive oxygen species; CL = Crosslinker.
[a]Lebrun et al., 2020.

Results

A limited set of chemicals were used to screen for the effects of tear antioxidants on FPs using approximate in vivo concentrations. FIG. 1 shows results for this study, which included a positive control (cyclohexanol) that remained far above the OPTISAFE (now called OS2) cutoff for GHS category 1 classification. Likewise, the negative control (2,4 pentanediol) remained below the cutoff for GHS NC classification. By. contrast, the FP, triethylene glycol, showed a significant reduction in the OPTISAFE (OS2) score in response to the addition of ascorbic acid (567 µM) resulting in a change of classification from a FP to a TN.

Based on the success of the screening study, a final formulation of antioxidant additives to the OPTISAFE (now called OS2) test kit was developed, and the effects on the OPTISAFE scores were further investigated with titrations and a broader range of FPs and controls. The exact formulation of the OPTISAFE assay is disclosed in U.S. Pat. No. 10,041,922B2; incorporated herein in its entirety. A set of materials associated with ROS, CL, "other FPs" (no association with ROS or CL identified), and positive and negative controls were selected to evaluate the final formulation. Results are shown in FIG. 2. Note that there is a specific reduction in the OPTISAFE (OS2) score at the in vivo concentration for each of the chemicals with associated ROS or CL activity. On the other hand, there was no significant change in controls or FP not associated with ROS or CL.

For OPTISAFE (OS2), the effective concentrations showing false positive reduction with the addition of ascorbic acid into the formulation begin at 0.270 mM and the maximal effect is shown at the in vivo concentration of 0.530 mM. This reduction of previously over-predicted chemicals was tested to be stable up to a concentration of at least 8.480 mM. The tested concentration range of ascorbic acid showing effectiveness in reducing false positives for in vitro assays was 0.27 mM to 17 mM. We predict, based on the data, that any ascorbic acid concentration within the range of 0.27 mM and 60 mM would be effective in reducing false positives; indeed, as long as the ascorbic acid is soluble and effectively buffered, there is no upper concentration limit.

Another set of experiments compared triplicate repeats for the formulation without and with antioxidants at the in vivo concentration. Table 4 shows these results for controls and Table 5 shows these results for ROS and CL chemicals. Controls were unchanged.

TABLE 4

OPTISAFE (original formulation without antioxidants) and OS2 (new formulation with antioxidants) Score Comparison of Control Antioxidant Titrations

| Chemical Name | GHS | Condition | OPTISAFE Score AVG | OS2 Score AVG |
|---|---|---|---|---|
| Cyclohexanol (108-93-0) | Cat. 1 | Pos. | 52.6 ± 1.1 | 66.9 ± 4.9 |
| 2,4-Pentanediol (625-69-4) | NC | Neg. | 12.0 ± 1.4 | 10.2 ± 0.7 |
| Dodecane (112-40-3) | NC | Neg. | 0.9 ± 0.8 | 3.0 ± 2.6 |
| Triphenyl phosphite (101-02-0) | NC | AO | 113.3 ± 2.1 | 169.0 ± 9.9 |
| Ethyl acetate (141-78-6) | NC | AO | 23.9 ± 2.0 | 25.6 ± 2.4 |
| 2,4-Pentanedione (123-54-6) | NC | NOT ROS/CL | 45.3 ± 1.4 | 42.3 ± 6.6 |
| 2,2-Dimethyl-3-pentanol (3970-62-5) | NC | NOT ROS/CL | 19.2 ± 1.2 | 15.1 ± 0.4 |

Scores of triplicate assays for FIG. 2 Control antioxidant titrations.
OS2 = OPTISAFE2, new and optimized version of OPTISAFE;
GHS = Globally Harmonized System of classification and labelling of chemicals;
Cat. = Category;
NC = Not classified;
Pos. = Positive control;
Neg. = Negative control;
AO = Antioxidant;
ROS = Reactive oxygen species;
CL = Crosslinker;
AVG = Average

TABLE 5

OPTISAFE and OS2 Score Comparison of ROS/CL Antioxidant Titrations

| Chemical Name | GHS (animal response) | Chem-istry | OPTISAFE (no anti-oxidant) Score AVG | OS2 (with anti-oxidant) Score AVG |
|---|---|---|---|---|
| 2-(2-Ethoxyethoxy)ethanol (111-90-0) | NC | ROS | 21.7 ± 0.3 | 12.0 ± 0.3 |
| Triethylene glycol (112-27-6) | NC | ROS | 13.2 ± 3.5 | 5.1 ± 1.7 |
| Ethylene glycol diethyl ether (629-14-1) | NC | ROS | 25.4 ± 1.8 | 21.6 ± 2.5 |
| Styrene (100-42-5) | NC | ROS | 53.5 ± 10.1 | 3.5 ± 0.8 |
| 1,9-Decadiene (1647-16-1) | NC | CL | 22.5 ± 3.6 | 11.4 ± 6.4 |
| 2-Ethoxyethyl methacrylate (2370-63-0) | NC | CL | 97.1 ± 18.2 | 14.5 ± 2.7 |

Figure 3:
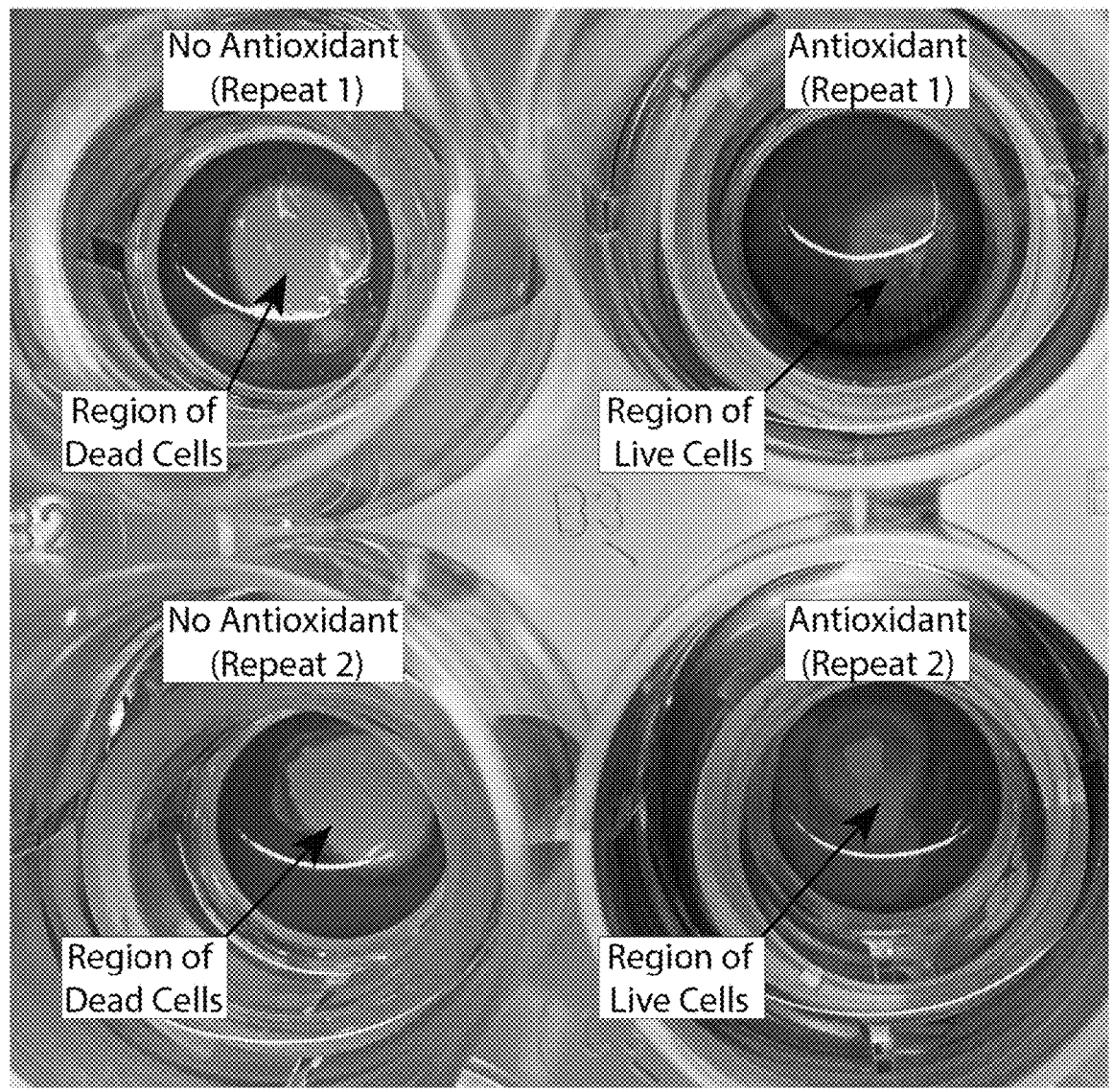
FIG. 3 depicts results from the modified EPIOCULAR reconstituted human corneal epithelium test system in which antioxidant formulation was added. Results from exposure to test substance (styrene) under two conditions, with or without antioxidant formulation (including 1.70 mM (0.3 mg/ml) ascorbic acid in a buffered salt solution) overlayed on the apical surface of the eye epithelial test model prior to addition of the styrene (in this case, the GHS NC chemical styrene).

Scores of triplicate assays for FIG. 3 ROS/CL.
OS2 = OPTISAFE2, OPTISAFE with antioxidants;
GHS = Globally Harmonized System of classification and labelling of chemicals;
NC = Not classified;
AO = Antioxidant;
ROS = Reactive oxygen species;
CL = Crosslinker;
AVG = Average On the other hand, all of the chemicals associated with ROS or CL had some reduction in score and most had an improvement in classification. As an example of this, we show for the first time that the addition of known antioxidants present in tears to the OPTISAFE (now called OS2) formulation reduces the OPTISAFE irritation score of FP chemicals that have oxidative or reactive chemistries. This finding suggests that a major drawback of many if not all in vivo alternative irritation tests is the failure to account for the effect of tears on modifying the irritation potential of test chemicals, particularly when they contain oxidative and reactive chemistries.

Results demonstrate that antioxidants specifically reduce the FP rates of chemicals associated with ROS and CL.

In order to demonstrate the effects of specific antioxidants and not increase the FN rate, a large number of chemicals from prior OPTISAFE (original formulation without antioxidants) validation studies were retested with the new OPTISAFE (OS2, formulation with antioxidants) formulation that includes antioxidants.

Next a study was conducted to determine if the addition of antioxidants changes the reliability (repeatability) of the test method. After this, a large study determined if antioxidants specifically reduce the false positive rate without impacting the true positive rate and the true negative rate and then all prior test chemicals were rested with antioxidants in triplicate. The OPTISAFE method was conducted as previously described (Choksi et al., 2020). Briefly, samples were initially evaluated for solubility, pH, and foaming using a standardized procedure. Based on the outcomes, a decision tree was followed to allow for standardized procedural modifications for substances with the following properties: 1) extreme pH, 2) insolubility, and 3) categorized as a surfactant.

Previous studies evaluated a range of antioxidants and enzymes associated with ocular antioxidant capabilities. The intralaboratory repeatability results are shown in Table 6. Three chemicals (1-octanol CASRN 111-87-5, 2,4-pentanediol CASRN 625-69-4, and triethylene glycol CASRN 112-27-6) were selected to assess the lot-to-lot repeatability of the new formulation with antioxidants. The three chemicals are representative of a negative control, a positive control, and an OPTISAFE (original formulation without antioxidants) overpredicted in vivo negative. The 10 independent repeats using different lots indicate the variability of both the classifications and scores. For the positive control, 1-octanol CASRN 111-87-5, scores ranged from 16.5 to 22.8 with an average of 19.1 and a standard deviation of 1.94. The negative control, 2,4-pentanediol CASRN 625-69-4, ranged from 7.8 to 10.9 with an average of 9.5 and standard deviation of 0.97. The scores of triethylene glycol CASRN 112-27-6, a previous FP identified as a potential ROS generator ranged from 2.1 to 4.2 with an average of 3.1 and a standard deviation of 0.64. These results indicate that the addition of antioxidants does not change the reliability of the test and the change from a FP to TN (see TG result) is consistent between numerous (10 lots) production lots and the effect is repeatable with low variability (standard deviation=0.64).

TABLE 6

Intralaboratory Repeatability of OS2 (new formulation with antioxidants)

| Lot # | OCT | PENT | TEG |
|---|---|---|---|
| 6.049975 | 22.8 | 10.1 | 3.9 |
| 6.049973 | 22.3 | 10.2 | 3.5 |
| 6.049971 | 18.6 | 10.1 | 3.1 |
| 6.049969 | 19.5 | 10.1 | 2.7 |
| 6.049967 | 19.9 | 8.0 | 4.2 |
| 6.049965 | 18.0 | 10.9 | 3.1 |

TABLE 6-continued

Intralaboratory Repeatability of OS2
(new formulation with antioxidants)

| Lot # | OCT | PENT | TEG |
|---|---|---|---|
| 6.049963 | 17.8 | 9.8 | 3.4 |
| 6.049961 | 16.5 | 7.8 | 2.5 |
| 6.049959 | 17.6 | 9.2 | 2.4 |
| 6.049957 | 18.3 | 8.8 | 2.1 |
| Score | 19.1 | 9.5 | 3.1 |
| Std Dev | 1.94 | 0.97 | 0.64 |

OCT = 1-Octanol (CASRN 111-87-5), in vivo GHS Category 2; PENT = 2,4-Pentanediol (CASRN 625-69-4), in vivo GHS NC; TEG = Triethylene glycol (CASRN 112-27-6), in vivo GHS NC; NC = Not classified; CASRN = Chemical Abstracts Service Registry Number; GHS = Globally Harmonized System of classification and labeling of chemicals; Score = Average score; Std Dev = Standard deviation.

In addition, the repeatability for a large number of tested chemicals was similar or better than the formulation without antioxidants. The intralaboratory repeatability of OS2 (new formulation with antioxidants) for the different studies ranged from 95.5% to 100% with a total repeatability of 96.7%. Comparatively, the intralaboratory repeatability of OPTISAFE (original formulation without antioxidants) was 93% to 99% for the coded transferability phase (Choksi et al., 2020). The intralaboratory repeatability OS2 (new formulation with antioxidants) for all results combined was 96.7%. Of the 426 assays run using OS2 (new formulation with antioxidants), 412 of the repeats were in agreement. This data demonstrates that for 10 different lots of the new formulation the test method is repeatable, and antioxidants do not change the reliability of the test method.

Next, to demonstrate that the addition of antioxidants only improves the false positive rate but does not change the TP or TN rates, a major study tested ALL prior OptiSafe validation chemicals in triplicate (OS2) and compared to the prior validation studies without antioxidant results (OS). These results are shown in Table 7.

Tables 7A and 7B Consensus OptiSafe Results Comparing Original Formulation (without Antioxidants) and OS2 (New Formulation with Antioxidants)

TABLE 7A

Past Transferability Study Classifications and Triplicate Repeats
OptiSafe Past Transferability Study Classifications and Triplicate Repeats by OS2

| n | Chemical Name (CASRN) | In vivo GHS | OS Cons[1] | OS2 R1 | OS2 R2 | OS2 R3 | OS2 Cons |
|---|---|---|---|---|---|---|---|
| 1 | 1,3-Di-iso-propylbenzene (99-62-7) | NC | 1 | 2/1 | 2/1 | 2/1 | 2/1 |
| 2 | n-Hexyl bromide (111-25-1) | NC | NC | NC | NC | NC | NC |
| 3 | iso-Octyl acrylate (29590-42-9) | NC | NC | NC | NC | NC | NC |
| 4 | Glycerol (56-81-5) | NC | NC | NC | NC | NC | NC |
| 5 | 1,9-Decadiene (1647-16-1) | NC | 2 | NC | 2 | NC | NC |
| 6 | Di-iso-butyl ketone (108-83-8) | NC | NC | NC | NC | NC | NC |
| 7 | 1-Bromo-4-chlorobutane (6940-78-9) | NC | NC | NC | NC | NC | NC |
| 8 | 1,6-Dibromohexane (629-03-8) | NC | NC | NC | NC | NC | NC |
| 9 | n-Octyl bromide (111-83-1) | NC | NC | NC | NC | NC | NC |
| 10 | Propylene glycol (57-55-6) | NC | NC | NC | NC | NC | NC |
| 11 | 2,4-Pentanediol (625-69-4) | NC | NC | NC | NC | NC | NC |
| 12 | Potassium tetrafluoroborate (14075-53-7) | NC | NC | NC | NC | NC | NC |
| 13 | 4,4-Methylene bis-(2,6-ditert-butyl)phenol (118-82-1) | NC | CNM | CNM | CNM | CNM | CNM |
| 14 | 2,2-Dimethyl-3-pentanol (3970-62-5) | NC | 2 | NC | 2 | NC | NC |
| 15 | 2-Methyl-1-pentanol (105-30-6) | 2B | 2 | 2 | 2 | 2 | 2 |
| 16 | Sodium chloroacetate (3926-62-3) | 2B | 1 | 1 | 1 | 1 | 1 |
| 17 | Isobutyraldehyde (78-84-2) | 2B | 1 | 1 | 1 | 1 | 1 |
| 18 | Camphene (79-92-5) | 2B | 2 | 2 | 2 | 2 | 2 |
| 19 | Ammonium nitrate (6484-52-2) | Cat 2A | 2 | 2 | 2 | 2 | 2 |
| 20 | 3,3-Dithiodipropionic acid (1119-62-6) | 2B | 1 | 1 | 1 | 1 | 1 |
| 21 | Isobutanol (78-83-1) | 2A | 1 | 1 | 1 | 1 | 1 |
| 22 | Dibenzyl phosphate (1623-08-1) | 2A | 1 | 1 | 1 | 1 | 1 |
| 23 | Propasol solvent P (1569-01-3) | 2A | 2 | 2 | 2 | 2 | 2 |
| 24 | Methyl cyanoacetate (105-34-0) | 2A | 1 | 1 | 1 | 1 | 1 |
| 25 | n-Butanol (71-36-3) | 1/2A | 1 | 1 | 1 | 1 | 1 |
| 26 | 3,4-Dichlorophenyl isocyanate (102-36-3) | 1 | 1 | 1 | 1 | 1 | 1 |
| 27 | p-Tert-butylphenol (98-54-4) | 1 | 1 | 1 | 1 | 1 | 1 |

The OptiSafe (original formulation without antioxidants) consensus result from the past transferability study (Choksi et al 2020), OS2 (new formulation with antioxidants) triplicate repeat data, and OS2 consensus data for the same chemical set is shown. In vivo GHS = GHS classifications based on the Draize data (the reference values); categories NC, 2A/B, 1 and IV are the decreasing irritancy categories determined through this system. R1, R2, R3, and Cons = repeats 1, 2, and 3, and consensus of the repeats. CNM = "criteria not met" due to internal quality assurance. OptiSafe and OS2 consensus are the majority prediction based on the triplicate assays conducted for each test method. OS = OptiSafe; CASRN = Chemical Abstracts Service Registry Number; GHS = Globally Harmonized System of classification and labeling of chemicals; NC = not classified; OS2 = OptiSafe2, new and optimized version of OptiSafe.
[1]Choksi et al., 2020.

TABLE 7B

Past OptiSafe (original formulation without antioxidants) Application Domain Study Classifications and Triplicate Repeats by OS2 (new formulation with antioxidants)
Past OptiSafe Application Domain Study Classifications and Triplicate Repeats by OS2

| n | Chemical Name (CASRN) | In vivo GHS | OS Cons[1] | OS2 R1 | OS2 R2 | OS2 R3 | OS2 Cons |
|---|---|---|---|---|---|---|---|
| 28 | Cyclopentasiloxane (541-02-6) | NC | NC | NC | NC | NC | NC |
| 29 | Ethylene glycol diethyl ether (629-14-1) | NC | 2 | 2 | 2 | 2 | 2 |
| 30 | Hexane (110-54-3) | NC | NC | NC | NC | NC | NC |
| 31 | 2-Ethylhexylthioglycolate (7659-86-1) | NC | NC | NC | NC | NC | NC |
| 32 | iso-Propyl bromide (75-26-3) | NC | NC | NC | NC | NC | NC |
| 33 | 1,2,6-Hexanetriol (106-69-4) | NC | NC | NC | NC | NC | NC |
| 34 | 3-Methoxy-1,2-propanediol (623-39-2) | NC | NC | NC | NC | NC | NC |
| 35 | Triethylene glycol (112-27-6) | NC | 2 | NC | NC | NC | NC |
| 36 | *Triphenyl phosphite (101-02-0) | NC | 1 | 1 | 1 | 1 | 1 |
| 37 | 2-Ethoxyethyl methacrylate (2370-63-0) | NC | 1 | 2 | 2 | NC | 2 |
| 38 | Hexamethyldisiloxane (107-46-0) | NC | NC | NC | NC | NC | NC |
| 39 | Hexyl cinnamic aldehyde (101-86-0) | NC | NC | NC | NC | NC | NC |
| 40 | p-Methyl thiobenzaldehyde (3446-89-7) | NC | 1 | 1 | 1 | 1 | 1 |
| 41 | Triclocarban (101-20-2) | NC | CNM | CNM | CNM | CNM | CNM |
| 42 | Ethyl acetate (141-78-6) | NC | 2 | 2 | 2 | 2 | 2 |
| 43 | 2,4-Pentanedione (123-54-6) | NC | 2 | 2 | 1 | 2 | 2 |
| 44 | Dodecane (112-40-3) | NC | NC | NC | NC | NC | NC |
| 45 | 2-(2-Ethoxyethoxy)ethanol (111-90-0) | NC | 2 | NC | NC | NC | NC |
| 46 | n,n-Dimethylguanidine sulfate (598-65-2) | NC | 2 | NC | NC | NC | NC |
| 47 | 1,4-Dibromobutane (110-52-1) | NC | NC | NC | NC | NC | NC |
| 48 | 3-Phenoxybenzyl alcohol (13826-35-2) | NC | 2 | 2 | 1 | 2 | 2 |
| 49 | Styrene (100-42-5) | NC | 1 | NC | NC | NC | NC |
| 50 | 1,5-Hexadiene (592-42-7) | NC | CNM | NC | NC | NC | NC |
| 51 | n,n-Diethyl-m-toluamide (134-62-3) | 2B | 2 | 1 | 1 | 1 | 1 |
| 52 | 3-Chloropropionitrile (542-76-7) | 2B | 1 | 1 | 1 | 1 | 1 |
| 53 | Isopropyl acetoacetate (542-08-5) | 2B | 1 | 1 | 1 | 1 | 1 |
| 54 | n-Butanal (123-72-8) | 2B | 1 | 1 | 1 | 1 | 1 |
| 55 | Ethyl-2-methyl acetoacetate (609-14-3) | 2B | 1 | 1 | 1 | 1 | 1 |
| 56 | Maneb (solid) (12427-38-2) | 2B | 1 | CNM | CNM | CNM | CNM |
| 57 | Isopropanol (67-63-0) | 2A | 2 | 2 | 2 | 2 | 2 |
| 58 | 2-Amino-3-pyridinol (16867-03-1) | 2A | CNM | CNM | CNM | CNM | CNM |
| 59 | Allyl alcohol (107-18-6) | 2A | 1 | 1 | 1 | 1 | 1 |
| 60 | Xylene (1330-20-7) | NC | NC | NC | NC | NC | NC |
| 61 | Cyclopentanol (96-41-3) | 2A | 1 | 1 | 1 | 1 | 1 |
| 62 | n-Hexanol (111-27-3) | 2A | 2 | 2 | 2 | 1 | 2 |
| 63 | gamma-Butyrolactone (96-48-0) | 2A | 2 | 2 | 2 | 2 | 2 |
| 64 | n-Octanol (111-87-5) | 2A | 2 | 2 | 2 | 2 | 2 |
| 65 | Methyl acetate (79-20-9) | 2A | 2 | 2 | 2 | 2 | 2 |
| 66 | 2,6-Dichlorobenzoyl chloride (4659-45-4) | 2A | 1 | 1 | 1 | 1 | 1 |
| 67 | Acetone (67-64-1) | 2A | 2 | 2 | 2 | 2 | 2 |
| 68 | Methylthioglycolate (2365-48-2) | 1 | 1 | 1 | 1 | 1 | 1 |
| 69 | Diethylaminopropionitrile (5351-04-2) | 1 | CNM | 2 | 1 | 1 | 1 |
| 70 | 6-Methyl purine (2004-03-7) | 2B | 2 or 1 | 2/1 | 2/1 | 1 | 2/1 |
| 71 | Imidazole (288-32-4) | 1 | CNM | 1 | 1 | 1 | 1 |
| 72 | Sodium perborate tetrahydrate (10486-00-7) | 1 | CNM | 1 | 1 | 1 | 1 |
| 73 | 2,5-Dimethylhexanediol (110-03-2) | 1 | 2 | 2 | 1 | 1 | 1 |
| 74 | Butanedioic acid, sulfo-, 1,4-bis(2-ethylhexyl) ester, sodium salt (577-11-7) | 1 | 2 | 2 | 2 | 2 | 2 |
| 75 | Cyclohexanol (108-93-0) | 1 | 1 | 1 | 1 | 1 | 1 |
| 76 | Lactic Acid (50-21-5) | 1 | 1 | 1 | 1 | 1 | 1 |
| 77 | Protectol PP (80-54-6) | 1 | 1 | 1 | 1 | 3 | 1 |
| 78 | Lauric acid (143-07-7) | 1 | 1 | 1 | 1 | 1 | 1 |

The OptiSafe (original formulation without antioxidants) consensus result from the past application domain study (Choksi et al 2020), OS2 (new formulation with antioxidants) triplicate repeat data, and OS2 consensus data for the same chemical set is shown. In vivo GHS = GHS classifications based on the Draize data (the reference values); categories NC, 2A/B, 1 and IV are the decreasing irritancy categories determined through this system. R1, R2, R3, and Cons = repeats 1, 2, and 3, and consensus of the repeats. CNM = "criteria not met" due to internal quality assurance. OptiSafe and OS2 consensus are the majority prediction based on the triplicate assays conducted for each test method. *Triphenyl phosphite CASRN 101-02-0, five total repeats were conducted for an overall prediction of GHS category 1. Only three of the repeats are shown. OS = OptiSafe; CASRN = Chemical Abstracts Service Registry Number; GHS = Globally Harmonized System of classification and labeling of chemicals; NC = not classified; OS2 = OptiSafe2, new and optimized version of OptiSafe.
[1]Choksi et al., 2020.

Table 8 shows a comparison of the accuracy (for the detection of GHS NC) of OPTISAFE (original formulation without antioxidants) and OS2 (new formulation with antioxidants). Based on the in-house retesting of chemicals from the prior validation study (transferability and application domain) for OS2 (new formulation with antioxidants), the FP rate for the GHS NC prediction improved from 40.0% for OPTISAFE (original formulation without antioxidants) to 22.2% for OS2 (new formulation with antioxidants). The FN rate for both remained the same at 0.0%, and the overall accuracy improved from 80.3% for OPTISAFE (original formulation without antioxidants) to 89.2% for OS2 (new formulation with antioxidants). This demonstrates the effect of antioxidants is specific to the reduction of the false positive (FN) rate; the false negative (FN) rate remained at 0 and accuracy improved from 80% to almost 90%.

TABLE 8

OptiSafe (original formulation without antioxidants) Coded Validation Study Results Compared with Repeat Testing by OS2 (new formulation with antioxidants)

| Statistics | [1,2]OptiSafe | OS2 |
|---|---|---|
| FN Rate | 0.0% (0/36) | 0.0% (0/38) |
| FP Rate | 40.0% (14/35) | 22.2% (8/36) |
| Accuracy | 80.3% (57/71) | 89.2% (66/74) |

OS = OptiSafe; OS2 = OptiSafe2; FN = false negative; FP = false positive. The values in parentheses denote the number of tested chemicals within each statistic over the total number of chemicals. The total n for OptiSafe and the n for OS2 do not match due to chemicals not meeting criteria of each test method. A full side-by-side review of the n's for OS and OS2 can be found in Table 3.
[1]Choksi et al., 2020.
[2]Lebrun et al., 2019.

The FN rate, FP rate, and accuracy for just the 12 surfactants was 0% (0/5), 16.7% (1/6), and 90.9% (10/11), respectively. Sodium lauroyl sarcosinate (10%) did not meet criteria (CNM) due to assay inhibition (see Choksi et al 2020). As shown in Table 9A, considering all results (including surfactants) for the prediction of the GHS NC classification, the FN rate was 0% (0/86), the FP rate was 20.8% (10/48), and the accuracy was 92.5% (124/134).

TABLE 9A

OS2 (new formulation with antioxidants) Repeat Testing of All OptiSafe (original formulation without antioxidants) Validation Studies and Additional Surfactants for the Detection of GHS NC

| Statistics | OS2 NC |
|---|---|
| FN Rate | 0.0% (0/86) |
| FP Rate | 20.8% (10/48) |
| Accuracy | 92.5% (124/134) |

GHS NC vs. 2, 1 analysis. Analysis includes all complied OS2 data (repeats of OptiSafe transferability study, repeats of OptiSafe application domain study, repeats of OptiSafe retrospective study, repeats of OptiSafe expanded corrosive study, and expanded surfactant study). The values in parentheses denote the number of indicated chemicals within each statistic over the total number of chemicals. OS2 = OptiSafe2, new and optimized version of OptiSafe; NC = not classified; FN = false negative; FP = false positive.

For the detection of ocular corrosives (GHS category 1), there were a total of 122 triplicate results. This is because 12 results predicted as either Category 2 or 1 (no differentiation between irritant and corrosive due to objective internal criteria) are not included in this analysis. As shown in Table 9B, the FN rate was 10.6% (5/47), with no GHS category 1 chemicals mispredicted as NC (all category 1 FNs were predicted as OHS category 2). The FP rate was 26.7% (20/75), and the accuracy was 79.5% (97/122).

TABLE 9B

OS2 (new formulation with antioxidants) Repeat Testing of All OptiSafe (original formulation without antioxidants) Validation Studies and Additional Surfactants for the Detection of GHS Category 1

| Statistics | OS2 Cat 1 |
|---|---|
| FN Rate | 10.6% (5/47) |
| FP Rate | 26.7% (20/75) |
| Accuracy | 79.5% (97/122) |

GHS Cat 1 vs. 2, NC analysis. Analysis includes all complied OS2 data (repeats of OptiSafe transferability study, repeats of OptiSafe application domain study, repeats of OptiSafe retrospective study, repeats of OptiSafe expanded corrosive study, and expanded surfactant study). The values in parentheses denote the number of indicated chemicals within each statistic over the total number of chemicals. OS2 = OptiSafe2, new and optimized version of OptiSafe; NC = not classified; FN = false negative; FP = false positive.

Comparison of OS2 (with Antioxidants) to Other In Vitro Ocular Irritation Tests

The performance of OS2 (new formulation with antioxidants) was compared to other test methods (without antioxidants) using OECD guideline statistics for the lowest (GHS NC) and highest (GHS Category 1) classification. For the GHS NC versus the rest comparison, OS2 (new formulation with antioxidants) has an accuracy of 92.5%, a false negative rate (FNR) of 0.0%, and a false positive rate (FPR) of 20.8% (Table 10A). For the GHS Category 1 versus the rest comparison, OS2 (new formulation with antioxidants) has an accuracy of 79.5%, a FNR of 10.6%, and a FPR of 26.7% (Table 10B).

Table 10. Comparison of OS2 (New Formulation with Antioxidants) with OECD Published Accuracies for BCOP (OPKIT), BCOP (LLBO), EPIOCULAR, ICE, OCULAR IRRITECTION and STE

TABLE 10A

| | | | GHS NC vs. Rest | | | | |
|---|---|---|---|---|---|---|---|
| OS2 | BCOP (OPKIT)[1] | BCOP (LLBO)[1] | Epi[2] | ICE[3] | OI[4] | STE[5] | |
| FNR = 0.0% (0/86) | FNR = 0.0% (0/107) | FNR = 6.3% (6.5/104) | FNR = 4.2% (2.4/57) | FNR = 3.0% (3/101) | FNR = 9.3% (4.3/46) | FNR = 12.3% (9/73) | |
| FPR = 20.8% (10/48) | FPR = 68.5% (61/89) | FPR = 45.1% (18.5/41) | FPR = 36.9% (20.3/55) | FPR = 24.1% (20/83) | FPR = 41.2% (17.7/43) | FPR = 19.3% (11/57) | |
| Acc. =92.5% (124/134) | Acc. = 68.9% (135/196) | Acc. = 82.8% (120/145) | Acc. = 79.6% (89.2/112) | Acc. = 87.5% (161/184) | Acc. = 75.3% (67.0/89) | Acc. = 8.6% (110/130) | |
| Bal. Acc. = 89.6% | Bal. Acc. = 65.8% | Bal. Acc. = 74.3% | Bal. Acc. = 79.5% | Bal. Acc. = 86.5% | Bal. Acc. = 74.8% | Bal. Acc. = 84.2% | |

[1]OECD, 2020a
[2]OECD, 2019a
[3]OECD, 2018
[4]OECD, 2019b
[5]OECD, 2020b

TABLE 10B

GHS Cat. 1 vs. Rest

| OS2 | BCOP (OPKIT)[1] | BCOP (LLBO)[1] | ICE[3] | OI[4] | STE[5] |
|---|---|---|---|---|---|
| FNR = 10.6% (5/47) | FNR = 13.8% (9/65) | FNR = 24.1% (13.5/56) | FNR = 46.7% (21/45) | FNR = 46.5% (9.3/20) | FNR = 51.3% (20/39) |
| FPR = 26.7% (20/75) | FPR = 25.4% (32/126) | FPR = 20.8% (18.5/89) | FPR = 7.1% (9/127) | FPR = 19.1% (13.2/69) | FPR = 1.2% (1/86) |
| Acc. = 79.5% (97/122) | Acc. = 78.5% (150/191) | Acc. = 77.9% (113/145) | Acc. = 82.6% (142/172) | Acc. = 74.7% (66.5/89) | Acc. = 83.2% (104/125) |
| Bal. Acc. = 81.4% | Bal. Acc. = 80.4% | Bal. Acc. = 77.6% | Bal. Acc. = 73.1% | Bal. Acc. = 67.2% | Bal. Acc. = 73.8% |

[1]OECD, 2020a
[2]OECD, 2019a
[3]OECD, 2018
[4]OECD, 2019b
[5]OECD, 2020b

Comparison of OS2 (new formulation with antioxidants) with other ocular test methods. Table 10A compares the statistics for classification of GHS NC versus Cat. 2 or 1. Table 10B compares the statistics of GHS Cat. 1 versus NC or Cat. 2. EpiOcular is unable to detect Cat. 1 chemicals and therefore is not listed on Table 7B (OECD, 2019a). OS2=OptiSafe2, new and optimized version of OptiSafe; GHS=Globally Harmonized System of classification and labeling of chemicals; BCOP=Bovine Corneal Opacity and Permeability; LLBO=Laser light-based opacitometer; Epi=EpiOcular; ICE=Isolated Chicken Eye; OI=Ocular Irritection; STE=Short Time Exposure; OECD=Organization for Economic Co-operation and Development; Cat.=Category; FNR=False negative rate; FPR=False positive rate; NC=Not classified; Acc.=Accuracy; Bal. Acc.=Balanced accuracy.
[1]OECD, 2020a
[2]OECD, 2019a
[3]OECD, 2018
[4]OECD, 2019b
[5]OECD, 2020b Table 10A and Table 10B compares OS2 (new formulation with antioxidants) with the stated OECD guideline accuracies for both the detection of GHS NC and GHS Category 1 or other tests (all without antioxidants). Balanced accuracy (Bal. Acc.) is included because the numbers of negatives and positives (shown in parenthesis) are variable and balanced accuracy provides an accuracy that accounts for true positives and true negatives equally. For the detection of NC versus the rest, the addition of oxidants significantly reduced the FPR as compared to the other tests except for the STE methods. However, the STE method has a much higher FNR. Reducing the FPR while maintaining a low FNR is an important consideration. Unless the FPR is low, it becomes unclear if positives are true positives or false positives, and this puts resistance to adopting nonanimal tests because safe products are erroneously classified as unsafe for the eye.

Previously, we demonstrated that the best way to compare one test to another is by comparing results for the same chemical (Lebrun et al., 2020). The comparison of OS2 (new formulation with antioxidants) with other test methods for the detection of GHS NC is shown in Table 11. When performance for the same chemicals is evaluated, OS2 (new formulation with antioxidants) has a comparatively higher accuracy than the other tests to which it was compared (without antioxidants) of around 90%. The FPR for the same chemicals is about ⅓ to ½ of compared to the other tests. This is consistent with the overall accuracy that resulted from the 131 results in triplicate. Also noteworthy, is the finding that the OS2 (new formulation with antioxidants) has a false negative rate of 0.0% (indicating the addition of antioxidants does not result in false negatives), compared to the other tests which have false negatives.

TABLE 11

Accuracy Comparison for the Same Chemicals between OS2 (new formulation with antioxidants) and BCOP (LLBO), BCOP (OP-KIT), EPIOCULAR, ICE, OCULAR IRRITECTION, STE

| Comparison | FNR | FPR | Accuracy |
|---|---|---|---|
| OS2 | 0.0 (0/54) | 20.0 (3/15) | 95.7 (66/69) |
| BCOP (LLBO) | 5.6 (3/54) | 33.3 (5/15) | 88.4 (61/69) |
| OS2 | 0.0 (0/65) | 30.8 (4/13) | 94.9 (74/78) |
| BCOP (OP-KIT) | 7.7 (5/65) | 38.5 (5/13) | 87.2 (68/78) |
| OS2 | 0.0 (0/66) | 16.0 (4/25) | 95.6 (87/91) |
| EpiOcular | 1.5 (1/66) | 32.0 (8/25) | 90.1 (82/91) |
| OS2 | 0.0 (0/32) | 42.9 (3/7) | 92.3 (36/39) |
| ICE | 3.1 (1/32) | 85.7 (6/7) | 82.1 (32/39) |
| OS2 | 0.0 (0/30) | 22.2 (6/27) | 89.5 (51/57) |
| OI | 6.7 (2/30) | 44.4 (12/27) | 75.4 (43/57) |
| OS2 | 0.0 (0/45) | 9.7 (3/31) | 96.1 (73/76) |
| STE | 24.4 (11/45) | 9.7 (3/31) | 81.6 (62/76) |

Comparison of same chemicals between OS2 (new formulation with antioxidants) and other ocular test methods. n = number of chemicals in common between the test methods compared; OS2 = OptiSafe2; new and optimized version of OptiSafe; BCOP = Bovine Corneal Opacity and Permeability; LLBO = Laser light-based opacitometer; ICE = Isolated Chicken Eye; OI = Ocular Irritection; STE = Short Time Exposure; FNR = False negative rate, expressed as %, number of positives misclassified as negatives[((FN)/(FN + TP)) · 100]; FPR = False positive rate, expressed as %, number of negatives misclassified as positives [((FP)/(FP + TN)) · 100]; Accuracy = total correct predictions divided by the n in common. [((TP + TN)/(TP + TN + FP + FN)) · 100]; TP = True Positive; TN = True Negative. Chemical results obtained from Lebrun et al., 2020; Lebrun et al., 2021 for same chemical comparisons between OS2 and the test methods.

Based on the dramatic reduction of the false-positive rate (from about 40% to 20%), without any increase in the false negative rate, we concluded that the addition of antioxidants to nonanimal tests is critical to lower the false-positive rate and have a high accuracy. This dramatic improvement is unexpected, and while nonanimal tests for eye safety have been done for 25 years, only now has the importance of the addition of antioxidants to these tests been recognized. The addition of antioxidants appears to be required for the accurate and specific modeling of eye safety after chemical or product exposure. This has never before been described with respect to in vitro, nonanimal test methods.

L-ascorbic acid is a water-soluble essential nutrient and is more highly concentrated in the tear film than in the serum. Its main functions are as an electron donor/antioxidant and cofactor for certain dioxygenases in epigenetic regulation (Han et al., 2021). Other roles in the human body include cell-signaling, as a hormone growth factor, and cytokine, including possibly via sodium-dependent vitamin C transporter 2 (SVCT) mediation of Janus kinase 2 (JAK), which promotes regulation of vitamin C in epigenetic modifications, and complex effects related to the regulation of cell pluripotency and differentiation (Han et al., 2021). Other functions include immune system modulation (Carr and Maggini, 2017).

Ascorbic acid induces collagen secretion and formation of cell sheets in the eye (human corneal cell culture; Grobe and Reichl, 2013). Ascorbic acid is a required cofactor for the hydroxylation of the amino acids proline and lysine required for collagen triple helix formation and stabilization, including in tissue repair (Levene and Bates, 1975; Grobe and Reichl, 2013; Peterkofsky, 1972). Collagen is critical to maintaining eye health and function; including the stroma (collagen I) and the basement membrane (collagen IV).

Because cell and excised eye assays could respond to ascorbic acid by altering cell growth, repair or other metabolic responses or possibly as a "nutritional response" (impacting the collagens etc.), as discussed above, it has been unclear (variables left undefined) if the ascorbic acid in tear, or added ascorbic acid, specifically inactivates reactive molecules and this prevents damage from occurring in the first place (versus the other types of responses mentioned above). On the other hand, the cell free macromolecular test system that we used specifically measures the level of molecular damage. By using a cell free test system, one can rule out effects on cell growth and repair, nutrition and possibly other complex yet to be defined variables related to cells and tissues; and more specifically determine if the mechanism of action is specific to the inactivation of ROS by direct chemical reduction (provides an electron to stabilize ROS). Therefore, the antioxidant provides immediate protection against ROS and other toxins. The response of a complex biological system is not required. However, because antioxidants such as ascorbic acid can buffer to extreme pH, and extreme pH in itself is damaging to the eye, these must be highly buffered (to between pH 6.5-7.5) before coming into contact with the eye. In our experience, HEPES, Tris and bicarbonate (for CO2 systems) are all effective buffers. In addition, the addition of dextran and albumin will improve the viscosity, retention time on the eye and osmolarity, ensuring that the antioxidant solution stays on the eye but does not dry out the eye causing additional damage while it remains (sticks) on the eye increasing the duration that the solution can interact (inactivate) toxin on the surface or that has penetrated into the tissue.

This formulation would be particularly effective after an accidental spill or other exposure to a strong oxidizer, which typically penetrate into the tissue. Likewise, in some formulations including make-up, cosmetics and personal care products (together, personal care products), preservatives and other toxins damage tissue by oxidation. Including this antioxidant mix in the formulation of the personal care product will likely decrease the irritating effects of the formulation by inactivating these reactive molecules before they damage the eye. In a similar fashion, eye drops and eye medications can contain preservatives and chemicals that increase penetration of the drug. These include benzalkonium chloride and other preservatives and agents that allow medications to penetrate into the tissue. By adding a buffered solution of ascorbic acid to the formulation, the reactive oxygen species are controlled resulting in less tissue damage and less of an adverse ocular effect. As explained above, the reduction in adverse effects is not related to complex biological response, it is related to the specific and immediate quenching of reactive chemistries by antioxidant electron donation. Per the examples provided, the specificity of the reaction can be verified using cell free eye irritation test; in this case, the substance being tested is predicted as an irritant because it damages macromolecules in a cell free test system without the antioxidant formulation. However, when the antioxidant formulation is added, the substance being tested is predicted to be a nonirritant by a cell free test system. This simple test will determine if the mechanism of action is simple chemical inactivation prior to damaging the tissue versus other complex nutritional or hormonal effects, etc.

Antioxidant Formulations

Formulations for Reducing False Positives for In Vitro Ocular Irritation Tests

In certain embodiments of the various in vitro ocular irritation test methods, an antioxidant formulation has been employed. That antioxidant formulation may utilize any combination of known antioxidants, and in some preferred embodiments, the formulation utilizes any one of more antioxidants found in tears (see e.g., Table 2). More particularly, antioxidants may be selected from ascorbic acid, baicalein, beta-carotene, bilirubin, caeruloplasmin, catechin, cobalamin, coenzyme Q10, cortisone, cryptoxanthin, crystallin, curcumin, cyanidin, delphinidin, epigallocatechin-3-gallate, esculetin, estradiol, estriol, folic acid, genistein, glutathione, glutathione peroxidase, human serum albumin, idebenone, kaempferol, L-acetylcarnitine, L-cysteine, lipoic acid, L-tyrosine, lutein, lycopene, melatonin, mexidol, myo-inositol, myricetin, N-acetyl cysteine, estrogen, omega-3, omega-6, omega-9, pelargonidin, peonidin, petunidin, piceatannol, pigment epithelium derived factor, quercetin, resveratrol, riboflavin, selenium, silymarin, superoxide dismutase, taurine, tempol, thiamine, thioredoxin, thymoquinone, transferrin, ubiquinol-10, uric acid, vitamin A, vitamin D3, vitamin E, and zeaxanthin.

Because metals may promote oxidation and/or generation of reactive oxygen species, the antioxidant formulation should have no metals in any valance state, including metal complexes (such as zinc ascorbate complexes). Accordingly, preferred embodiments of the formulation do not comprise any metals, including in particular, iron, silver, magnesium, zinc, and copper.

Antioxidants, such as ascorbic acid, serve the purpose of reducing oxidative injury within biological systems through quenching of free radicals (Gulcin, 2020). In contrast, metals cause reduction-oxidation cycling reactions which causes damaged. Through the Fenton reaction, metals, such as iron, promote oxidation and the production of free radicals; ultimately, this results in biological injury (Winterbourn, 1995). Specifically, the Fenton reaction produces hydroxyl radicals from hydrogen peroxide and an Iron (II) catalyst. While the inclusion of antioxidants is aimed to target this oxidative stress, there is a point in which the "increased formation of reactive oxygen species (ROS) overwhelms body antioxidant protection and subsequently induces DNA damage" (Jomova and Valko, 2011). These metals include iron (Fe), copper (Cu), chromium (Cr), cobalt (Co) and other metals (Jomova and Valko, 2011). Furthermore, the addition of metals is counterproductive to the initial objective. The point of interest is oxidative stress mediation; the disclosed embodiments do not align with the addition of metals, and indeed, we teach away from this.

In some embodiments, the antioxidant formulation comprises one or more compounds selected from glutathione (about 1.0-107 μM), L-cysteine (about 0.5-5,000 μM), L-tyrosine (about 0.5-5,000 μM), ascorbic acid (about 0.27-60 mM) and uric acid (about 3.0-30,000 μM). L-ascorbic acid (0.3 mg/ml and 3 mg/ml) has been used for the experiments disclosed herein.

Besides antioxidant(s), the antioxidant formulation will preferably also include serum albumin (or other serum protein). Albumin itself has antioxidant properties, and also promotes lipophilic chemical transport and binding properties, osmotic properties, protects cells, and can interact with toxins. The albumin concentration is between 0.05% and 10% w/v; more preferably 0.1% to 5% w/v. Although 1% w/v bovine serum albumin was used for the experiments disclosed herein, any other species albumin, and concentrations within the disclosed ranges, may be used in accordance with the disclosed and claimed invention.

Besides antioxidants and albumin, the formulation also includes dextran. Dextran has osmotic properties, prevents drying out, improves viscosity and ensures the antioxidant/protein solution maintains a film over the tissue. Preferably, the dextran is present in a concentration of between about 3% and 30% w/v, and more preferably at a concentration of at least about 5% w/v. Although 5% w/v dextran was used for the experiments disclosed herein, any other concentrations within the disclosed ranges may be used in accordance with the disclosed and claimed invention.

The antioxidant formulation is dissolved in a salt buffer system, adjusted to a neutral pH, preferably between about pH 7 and pH 7.5. The buffer may be any buffer used in the art, such as HEPES, Tris or bicarbonate buffer, all of which work well in this pH range. Sodium chloride should be added to provide osmolarity mirroring that of physiologic tears, typically normal saline; 6 mg/ml NaCl was used in these studies.

Other ingredients, including thickening agents, such as carboxymethyl cellulose, moisturizer/humectant/emollient, such as glycerin, and preservatives (although antioxidants are also useful as preservatives against oxidative damage), such as benzoic acid, benzyl alcohol, benzalkonium chloride, etc., may also be added, particularly if an antioxidant formulation is formulated for sale and storage at room temperature.

While the antioxidant formulation has been demonstrated to reduce false positive rate in the in vitro nonanimal ocular irritation test systems, it is also envisioned that the same formulation may be used in vivo as a countermeasure to acute exposure to eye irritants, such as mustard gas.

Formulations for Mitigating In Vivo Damage after Irritant Exposure

In certain embodiments, the antioxidant formulation developed for reducing false positives and enhancing accuracy of in vitro eye irritation tests, can be modified for treating exposure to eye irritants, such as a countermeasure against chemical assault or after accidental exposure such as a chemical splash. The results above for use in in vitro tests demonstrate that physiologic levels of tear antioxidants protect eye tissues (reconstituted and excised eye models) from oxidizers, crosslinkers and reactive oxygen species. The presence of antioxidants (in tears) are a key difference between in vitro nonanimal tests and live animals, where tears protect the live animal eye naturally allowing some chemicals to be classified as nonirritants, we hypothesized that increasing the concentration of these antioxidants above physiologic levels by the external application of a supplemental high antioxidant tear solution, will protect the eye from higher concentrations of chemical irritants, and therefore protect against more severe oxidative damage. Accordingly, the proposed formulations, where antioxidant concentrations are substantially increased, are likely to have utility for the protection from and first aid following contact of the eye with strong oxidizers, crosslinkers and chemicals that generate reactive oxygen species. To test this hypothesis, we added antioxidant formulations with and without high concentrations of ascorbic acid (17.0 mM; 3 mg/ml; 10-fold higher than used for the in vitro studies) in a reconstituted human corneal epithelium (RhCE) model system. With reference to FIG. 4, it can be seen that the high levels of ascorbic acid (3 mg/ml (17.0 mM) in a buffered salt solution) afforded significant protection against damage (cell death) caused by a variety of damaging chemical irritants, compared to buffered salt solution alone. The other constituents of the high concentration antioxidant formulation for in vivo post-exposure protection will be essentially the same as the in vitro formulation, e.g., albumin and dextran, and optionally moisturizers/humectants, thickening agents, preservatives.

EXPERIMENTAL DETAILS AND EXAMPLES 1.1 Additions of Eye Antioxidants to Biochemical Test The addition of antioxidant mixtures can be done into the biochemical test matrix or added to sample to be tested. This is done easily through introduction of a specified amount to the reagent, followed by solubilization into the reagent, for example by using a metal stir bar and magnetic mixing plate for an allotted amount of time. The homogenous mixture is then used for the assay as normally conducted. One or more of the following antioxidants were used for final antioxidant mixture; GSH, L-cysteine, L-tyrosine, ascorbic acid, and uric acid. The procedure was:

Pretest and Surfactant Check
1) Make "10% dilution" of substance in screw cap glass test tubes in 2 mL OSII™ Blanking Buffer (BB) by adding 200 μL/200 mg test sample into a screw-cap glass tube.
2) Add 2 mL of the pH-adjusted BB to labeled tube [for colored test samples, adjust the pH of the BB to 6.36 using dilute (0.1 N, etc.) NaOH or dilute (0.1 N, etc.) HCl].
3) Cap tube and invert three times. Vortex mix at 45-degree angle at maximum speed for 10 sec.
4) Place tubes in a rack on bench top and allow the tube to sit undisturbed for 5-10 min.
5) Inspect tube; pick up and hold to light. If all of the substance is at the meniscus and blocks the observation, repeat the procedure at a 1% dilution if needed. Measure from the meniscus up using a metric ruler. If froth extends greater than 0.2 cm above the meniscus and bubbles are present (in either tube), the substance is classified as a "surfactant" using this method.
6) Inspect the 10% tube from the sides and bottom. If the substance is a liquid and has not mixed with the OSII BB, starts to form "oily" droplets at the top or middle or bottom, or is unclear whether the substance is mixed (all clear liquids), conduct the Δ procedure (in addition to the α procedure).

Completely Insoluble Check
1) If the substance is a solid, let the 10% solution (made above) sit undisturbed for 30 min (up to 4 h). Note if the substance is a solid and the majority floats to the top ("F"), aggregates in the middle ("A"), or sinks ("S") to the bottom of the tube; note this and remove approximately 0.5 mL of the liquid portion (and avoid solid portion) using a 1-mL serological pipette. Record this in procedure notes section.
2) Set the spectrophotometer to 400 nm and blank.
3) Measure the OD400 of the recovered solution.

4) If the substance is a solid and the measured value is less than 0.350, follow the 42-h completely insoluble protocol. See Section Ci if the substance floats/aggregates/clumps or sinks.
5) If the OD is greater than 0.350, the substance is not completely insoluble.

H Buffering Score Pretest
1) Measure the buffering power of an unknown and calculate the H-buffering score by adding a 125 µL or, if solid, a 125 mg (±10%) aliquot of test sample into a 7-mL tube.
2) Select the 8 mL tube of frozen Active Agent (AA). Use a 10-mL beaker with "mini" stir bar. Prepare the small vial of the pH-adjust solution by adding 2.5 mL deionized water and invert/shake 5-8 times. Optional: Dilute the pH-adjust solution 1:3 and/or 1:10 in deionized water (if needed for fine pH adjustments).
3) Record the starting pH of the AAII (6.36) on the pre-test data sheet.
4) Add 1.25 mL of pH-adjusted AA into a plastic 7-mL tube.
5) Cap tube and vortex mix for 5 sec at maximum speed.
6) Place tube on bench top and allow it to sit for 5 min±30 sec. In cases where the solution pH does not stabilize, continue incubation until the pH stabilizes; record this pH value and note the time until pH stability reached.
7) Measure and record the final pH on the pre-test data sheet.
8) Subtract the final pH from the starting pH. Use this absolute value as the exponent (base 10). Add a sub A or B to indicate acidic or basic buffering. The resulting value is the H-Buffering Score.
9) If the resulting H-Buffering Score is: Less than 5.0A or 2.0B, the substance is within the MA or Ci (floats/aggregates or sinks) application domains; Not MA but less than 100A or 100B, the substance is within the *HMA application domain; Greater than 100A or B, then follow the H procedure. (*Note: In the event a test substance is both completely insoluble and the H score is less than 100.0 but greater than 5.0A or 2.0B, use best scientific judgment to select one or the other.)

Alpha Procedure
1) Pre-weigh solid test samples and place membrane discs before starting.
2) Adjust the pH of the BB to 6.36 using NaOH. (Only required for colored test samples.)
3) Remove the 40-mL tube of frozen AAII solution from the freezer. Record the lot number and then warm the AAII solution in a 26-28° C. water bath. The water level should be the same height as the AAII within the tube. The AAII should sit in the water bath for 40 min (50 min maximum).
4) Transfer the AAII to a 50-mL beaker with a stir bar. Allow good vortexing but minimal foaming. Add the antioxidant mixture at a specified concentration. Calibrate the pH meter and confirm its functionality by comparing measurements with a second calibrated pH meter. Record the initial pH. Reconstitute the larger aliquot of the pH-adjust solution. Add 10 mL of deionized water and screw the cap tight. Shake/invert 5-8 times. Use immediately; this mixture is single use only.
5) Slowly add the specified amount of antioxidant mixture to the AAII using a stir bar and magnetic plate to incorporate. Allow mixing until completely solubilized. Note any changes for quality assurance records. (Optional: Pre-add the antioxidant mixture to the AAII before freezing the initial lot of AAII. Follow step 5 to incorporate into reagent.)
6) Adjust the pH to exactly 6.36 using the re-constituted pH-adjust solution: add dropwise and do not overshoot. When close to the desired pH value, allow at least 10 sec between drops to ensure equilibrium is reached. A pH adjustment will typically take 5-10 min and should not exceed 15 min.
7) Label the provided 24-well plates (when multiple tests of the same type are performed at the same time, only one set of standards plate is used).
8) Pipette 1.25 mL BB solution into the corresponding labeled 24-well-plates with a 12.5-mL Eppendorf Combitips (or equivalent).
9) Pipette 1.25 mL of pH-adjusted (6.36) AAII solution into the corresponding labeled 24-well plates with another 12.5-mL Eppendorf Combitips.
10) If the substance is a solid with a pretest solubility check greater than 0.350, or a liquid, place membrane discs into each well (if solid, this should already have substance within it). Carefully lift the 24-well plates and check the bottom to make sure there are no bubbles between the contacting membrane and solutions. Gently tap the side of the plate or lift the discs to get rid of any bubbles.
11) Label each plate on the top and side using a Sharpie pen. Optional: Label the lid of each 24-well plate as indicated above and place the respective lid above the 24-well plates to be used as a guide. For liquid samples, doses of 25 µL, 50 µL, 75 µL, 100 µL, and 125 µL will be used. For solid samples, doses of 50 mg, 100 mg, 150 mg, 200 mg, and 250 mg will be used.
12) Pipette 125-4 triplicates of standard 0 into three wells: triplicate standard IV, triplicate of Standard III, and singles of QC 1 and QC 2 into the appropriate wells.
13) Pipette 25, 50, 75, 100, and 125 µL of the unknown test sample into the appropriate BB and AA wells.
14) Pipette 125 µL (or 250 mg if solid, pre-weighed) of the test sample into the wells labeled TN+ and TNB.
15) Add 125 µL TN for liquid samples or 250 µL TN for solid samples to the three wells on the left side labeled TN+, TN−, and TNB (directly to center of well). If solid, mix substance with pipette tip to ensure at least some of the solubilized test substance is in contact with the membrane at the bottom of the sample well.
16) Place each 24-well plate in container provided. Seal the container by pressing firmly on all edges and then along the entire edge of box. Replace damaged incubation boxes that do not form good seal.
17) Place the entire container in a 30.6-31.3° C. incubator and set a timer for 18 h. Incubation time should be 18-19 h (optimum 18 h, time is allowed when conducting multiple assays at the same time).

Reading the 400 nm (a) Assay Results
1) Turn on the spectrophotometer for at least 10 min before use.
2) Adjust the spectrophotometer to 400 nm, absorbance mode. Press "esc," Press "General Tests," Press "Basic ATC," Press "Set Wavelength," enter "400," and then press "enter." If not in absorbance mode, press "mode." Adjust to absorbance mode. Readout should include "A" at the end.
3) Blank the spectrophotometer: Add 1 mL BB solution to a cuvette, place in the spectrophotometer, and push the blank button. The spectrophotometer should read "0.000A" (+/−0.002).

4) After the assay incubation time is complete, remove the plate from the incubator; remove the ocular discs from each well and dispose of them appropriately. Check each disc for damage. Make a record of damaged discs or any other abnormality (precipitate, color, etc.). Fluid in the disc is normal; it is related to denaturation via osmotic forces.

5) Mix the solution in each well individually with the tip of a 1-mL pipette prior to measuring the OD. This involves rapidly and forcefully scraping the bottom of the well with a standard size 1-mL pipette tip five times in one direction (in rapid zig-zag pattern), scraping the tip around the bottom edge 2-3 times, and then repeating two more times (for a total of three) to solubilize any white precipitate that has formed on the bottom of the well of the 24-well plate. Mix with force and attempt to hear an audible scraping sound (not possible with some viscous fluid samples). The precipitate at the bottom may not be visible. The precipitate at the bottom does not readily go into solution. Forceful and complete mixing is required for accurate results. After mixing, immediately aspirate the solubilized solution from the center bottom of the well.

6) Immediately aspirate 500 µL into a test cuvette after mixing. Tap the cuvette on the bench top to allow any bubbles to rise to the surface.

7) Immediately measure the OD at 400 nm using a recently blanked (with BB) spectrophotometer.

8) Include negative values on the data capture sheet.

9) Record the result and any notes on the data capture sheet. (If readings fail to stabilize, consult the supplier for additional procedural information).

Data Analysis

1) Sample OD values are recorded under the column "Sample OD" for each respective concentration.

2) Blank OD values are recorded under the column "Blank OD" for each respective concentration.

3) Measured values (MV=Net OD values) are obtained by subtracting the Blank OD value and the average standard 0 OD value from the Sample OD values for each respective concentration. (Note: if less than zero, enter 0.)

4) Standard value (SV) is obtained by subtracting the average standard 0 value from the average of the measured values for the standards.

5) For each measured unknown test value (MV), assign a numerical value ("score") by using the closest standard value (CSV).

6) Identify the standard with the closest OD value (either standard IV or III). Divide the measured OD by the closest standard value (MV/CSV) and multiply this value by the CSV designation (DV) (either IV=8.0 or III=12.5).

7) The resulting value=irritation score for the sample in question. Populate the template with both OD values and irritation scores.

8) Calculate the TN Value: Subtract both the TNB OD and the TN− OD from the TN+ OD.

9) Calculate the irritant score for the TN following steps above. If the TN score is the highest score, base the irritancy prediction on the TN score using the prediction models. Disregard negative TN Measured values and scores.

10) For the assay results (25-125 titrations) and the TN, convert the calculated irritation scores into EPA and GHS categories using the prediction models. Only the highest score (including TN) is used for the final prediction.

11) The FP rate was significantly less when the antioxidant mixture was used. The reduction of overpredicted nonirritants is attributed to the ability of the antioxidant mixture to quench the reactivity of nonirritant chemicals. 2,2-dimethyl-3-pentanol CASRN 3970-62-5 (GHS NC, EPA III), 2-ethylhexylthioglycolate CASRN 7659-86-1 (GHS NC, EPA IV), and isopropyl bromide CASRN 75-26-3 (GHS NC, EPA IV) were all overpredicted, but were corrected with the addition of the antioxidant mixture to reflect the GHS classification of NC.

1.2 Additions to Tissue Culture Media for EPIOCULAR, STE, and Other Cell- or Tissue-Based Tests for Ocular Toxicity To include the antioxidant mixture in cell-based assays, the mix can be added to the medium or the test sample. Per the EPIOCULAR protocol by MatTek Corporation, the EpiOcular Assay Medium should be warmed to approximately 37° C. The antioxidant mixture, containing one or more of the following: GSH, L-cysteine, L-tyrosine, ascorbic acid, and/or uric acid, is added to and solubilized in the medium until a homogenous mixture is reached. The tested range of ascorbic acid concentration included in the EPIOCULAR test method was from 1,703.4 to 17,033.8 µM. Following this, 1.0 mL of Assay Medium is aliquoted into the appropriate wells of pre-labeled 6-well plates, the tissues should be removed from the 24-well plates, and the insert is then transferred into the 6-well plates and preincubated in the Assay Medium (MatTek Corporation, 2021). Similarly, the antioxidant mixture can be applied to the media for the STE test method (ICCVAM-NICEATM, 2013). The standard operating procedures are listed as follows:

Modified EPIOCULAR—The following procedures were adapted from EPIOCULAR Eye Irritation Test (OCL-200-EIT) (2021) by MatTek Corporation (Available at: https://www.mattek.com/wp-content/uploads/OCL-200-EIT-Eye-Irritation-Test-Protocol-MK-24-007-0055_02_02_2021.pdf). Some procedures are from the MatTek EpiOcular Eye Irritation Test (OCL-200-EIT) Protocol. Additional new steps to the procedure are included as steps 2, 14, 15, 17, 18, 19.

Tissue Preincubation

1) RhCE tissues (purchased from MatTek Corporation) are equilibrated for about 15 min.

2) The antioxidant is added to the Assay Medium and used for all steps that follow and/or the antioxidant is added to the test chemical or overlayed over the tissue prior to test chemical exposure. Antioxidant procedure: 2.7 mg of the antioxidant (Ascorbic acid, CASRN 50-81-7) was added to 10 mL of the EpiOcular kit's media (OCL-100-ASY, Lot No. 021821TTC), mixed with a stir bar for 5 minutes, and the pH was adjusted using Sodium hydroxide (NaOH, CASRN 1310-73-2) or Hydrochloric acid (HCl, CASRN 7647-01-0).

3) The DPBS was prepared in two beakers of 100 ml. In beaker A, 27.2 mg of Ascorbic acid was added, mixed with a stir bar for 5 minutes and the pH was adjusted to 7.35 using HCl or NaOH. In beaker B, 20.1 mg of Ascorbic acid was added, mixed with a stir bar for 5 minutes and the pH was adjusted to 7.37 using HCl or NaOH.

4) Cell culture medium was warmed to approximately 37° C. and one mL aliquoted into the appropriate wells of 6-well plates.

5) Tissues were removed from the shipping containers forceps and then into the 6-well plates and incubated at standard culture conditions for 1 h, then assayed medium changed and incubated overnight (16-24 h).

Test Substance Exposure
1) Antioxidant procedure: During this Pre-Treatment step, 100 μL of DPBS (without Ascorbic acid) was added to tissues of Condition 1 (no Ascorbic acid added) and 100 μL of DPBS (with Ascorbic acid) was added to tissues of Condition 2 (with Ascorbic acid added).
2) Test Article Exposure: After the 30±2-min pretreatment with and without ascorbic acid, each test is tested by applying 50 μL topically. The tissues were then incubated at standard culture conditions for 30±2 min.
3) Antioxidant procedure: The test article used was Styrene (CASRN 100-42-5, Lot No. MKCM4502). 50 μL of styrene was added to the tissue inserts of Conditions 1 (no Ascorbic acid added) and 2 (with Ascorbic acid added).
4) Rinsing: At the end of the 30-min test chemical exposure time, the test articles are removed by rinsing the tissues.
5) Antioxidant procedure: Tissue inserts of Condition 1 (no Ascorbic acid added) were rinsed using DPBS (no Ascorbic acid added) and tissue inserts of Condition 2 (with Ascorbic acid added) were rinsed using DPBS (with Ascorbic acid added).
6) Antioxidant procedure: After rinsing, the tissue inserts of Condition 1 (no Ascorbic acid added) were immersed into 5 mL of the media without Ascorbic acid added and tissue inserts of Condition 2 (with Ascorbic acid added) were immersed into 5 mL of media for 60 minutes with Ascorbic acid added for 60 minutes.
7) Antioxidant procedure: After the 60 minutes of immersion, the tissue inserts of Conditions 1 (no Ascorbic acid added) and 2 (with Ascorbic acid added) were removed and placed into the 6-well plate containing 1 mL of the corresponding media (with or without Ascorbic acid) for another 60 minutes. The tested range of ascorbic acid included in the EPIOCULAR test method is from 1,703.4 to 17,033.8 μM.

Modifications Required for Solids
1) Each solid is tested by applying one leveled volumetric spoonful of material to be tested into tissue insert (approximately 50 mg). and incubated for 6 hours.
2) Rinsing: At the end of the 6 hours, the test articles are removed by rinsing (as above).
3) Post-treatment: After rinsing, the tissue inserts are immersed in 5 mL of previously warmed Assay Medium
4) Recovery: Next, each insert is removed from the Assay Medium, and transferred to a plate containing 1 mL of Medium. The tissues are then incubated for 18 hours under cell culture.

Cell Viability Test
1) After the post-treatment incubation, the MTT viability test is done.
2) A 1.0 mg/mL MTT solution is prepared and 300 μL of the MTT solution is added to each well of a 24-well plate. each insert is removed from the 6-well plate and placed into the 24-well plate containing 0.3 mL of MTT solution. The plate is then incubated for 3 hours under culture conditions.
3) After incubation, each insert is removed from the 24-well plate and then transferred to a 24-well plate containing 2.0 mL of isopropanol. The plates are sealed with saran wrap and are either stored overnight with refrigeration. After this, tissue inserts are pierced and the liquid is decanted into the well from which it came.
4) The extract solution is mixed and two 0.2 mL aliquots from each well transferred into a 96-well plate.
5) The absorbance at 570 nm (OD570) of each well is measured with a plate reader.
6) If the MTT OD570 is 60% or greater of that generated by the negative control, the material tested is classified as a nonirritant. On the other hand, if the test substance OD570 is less than 60% of the negative control, the test material is considered an ocular irritant.

Alternative Visual Determination of Viability and Irritant Prediction
1) Since viable cells turn MTT purple, the relative viability of one tissue to the next can be determined by a visual inspection. The more purple the more alive the cells and the less irritating the test substance applied to the cells are. For example, a large area of white indicates a lot of cell death and an irritating substance. On the other hand, a small area of white or areas of color indicate less cell killing (higher cell viability) and a less irritating test substance.
2) If the purple area is 60% or greater, the material tested is a classified as a nonirritant. On the other hand, if the purples area is less than 60% the test material is considered an ocular irritant.
3) The addition of the antioxidant mixture into the tissue medium has the potential to reverse the overprediction of the known FPs that have been tested by EpiOcular. A real example is provided for styrene, a current overpredicted irritant of the EpiOcular test, suggests that the correct nonirritant classification will result when the antioxidant mixture is introduced into the cell-based assay. As shown in FIG. 3, when the above procedure was followed, application of the FP chemical styrene resulted in extensive cell killing (condition 1, indicated by the large area of white, where there are no viable cells). However, when ascorbic acid (0.3 mg/ml) was added to the PBS overlay and culture medium, there was significantly less cell killing (Condition 2, area of dark, showing viable cells), and a prediction of nonirritant (TN). This indicates that the addition of the antioxidant results in a reduction of the rate of false positives and an increase in test method specificity and accuracy.
4) In summary, results for the novel addition of antioxidants described above, are shown in FIG. 3. The viability of cells is observed or quantified using MTT (3-[4,5-dimethylthiazol-2-yl]-2,5-diphenyltetrazolium bromide) treatment, which is a dye that forms a blue/purple color when reduced (through continued redox cycling of living cells). In Repeat 1 and Repeat 2 of the "No Antioxidant" condition (Condition 1) on the left side, there is a visually clear region of dead cells after treatment with Styrene. There is no color in the region of dead cells between MTT is not reduced. In this condition, no Ascorbic acid was added to the DPBS or media when following the antioxidant procedure. In Repeat 1 and 2 of the "Antioxidant" condition (Condition 2) on the right side, there is a region of live cells after treatment with Styrene. The region of live cells is a blue/purple color which indicates that MTT is being reduced and the cells are viable. The only difference is, in this condition, an antioxidant was added to the DPBS and the media. Overall, based on the results and the clear distinction between the region of dead cells and region of lives cells in both conditions, it can be concluded that the antioxidant procedure with this RhCE procedure produced a significant increase in viability, and therefore, the false positive styrene, is no longer a false positive when antioxidants are added. This result is consistent with the results for the addition of antioxidants to the OptiSafe test.

Using a Buffered High Concentration Ascorbic Acid Formulation for Preventing Corneal Damage Following Exposure to Irritant—Modeled in the Modified EPIOCULAR Test System FIG. 4 depicts results from the modified EPIOCULAR reconstituted human corneal epithelium test system (details of assay above) in which a high concentration antioxidant in a buffered salt solution was added. After exposure to known irritants (D, E, F) or nonirritant controls (A, B, C) transiently to mimic an accidental exposure into the eye, the ocular tissues were washed with the buffered salt solution without ascorbic acid (left column) or with a high concentration (17.0 mM; 3 mg/ml) ascorbic acid (right column). The dark staining is associated with viable cells in the corneal epithelium—i.e., greater protection against damage. This experiment demonstrates what would be expected when an ocular irritant contacts the eye in vivo, and the eye is then washed/flushed as a first aid measure to reduce damage to the eye tissue. The addition of the high concentration ascorbic acid to the buffered salt solution wash significantly reduced the corneal damage (evidenced by higher cell viability—dark staining) caused by known irritants, compared to the cellular damage (evidenced by extensive cell death—very little staining) in reconstituted corneal tissue washed with the same buffered salt solution without any added antioxidant; compare the dark stained areas (viable cells) seen in the ascorbic acid group with the light, translucent areas (dead cells) seen in the group without antioxidant. Death of eye tissue is associated with irritation and/or scarring and permanent eye damage. Thus, buffered high concentration antioxidant appears to be highly effective in mitigating corneal damage caused by chemical irritants.

STE—The procedures are available from the NICEATM Review Document (2013) Short Time Exposure (STE) Test Method Summary Review Document (Available at: https://ntp.niehs.nih.gov/iccvam/docs/ocutox_docs/ste-srd-niceatm-508.pdf). Additional steps are included as steps 1 and 2.

1) Prepare Medium. Add a specified amount of the antioxidant mixture to the media and allow to completely solubilize. For best results, use a stir bar and magnetic plate to slowly stir. Once the homogenous solution is obtained, proceed using medium with the incorporated antioxidant mixture through the assay. Alternatively, add the antioxidant to the chemical to be tested, or overlay the tissue with antioxidant medium prior to test chemical exposure.

2) Alternatively, add the antioxidant to the chemical to be tested or overlay the tissue with antioxidant medium prior to test chemical exposure. Start by preparing the media (MEM) and add a specific amount of the antioxidant mixture to the media and allow it to completely solubilize. For the best results, use a stir bar and a magnetic plate to slowly stir until homogenous. If necessary, adjust the pH using Sodium hydroxide (NaOH, CASRN 1310-73-2) or Hydrochloric acid (HCl, CASRN 7647-01-0). Once the homogenous solution is obtained, proceed using MEM with the incorporated antioxidant mixture throughout the entirety of the assay.

3) The inclusion of the antioxidant mixture in the media for STE allows for a reduction of FP chemicals predicated by the cell-based assay. In the prophetic analysis of styrene, a GHS NC, the novel addition to the STE assay is projected to reclassify this chemical. The antioxidant mixture is indicated to increase the measured cell viability to correctly categorize ethyl acetate as a TN.

1.3 Adding to Media for BCOP, ICE, IRE (Isolated Rabbit Eye), and any Other Ex Vivo Eye Test System, Including Human Addition of the antioxidant mixture for ex vivo assays such as BCOP, ICE, IRE, etc. can be to the media or substance to be tested. The final antioxidant mixture includes one or more of the following: GSH, L-cysteine, L-tyrosine, ascorbic acid, and/or uric acid. For BCOP, the preparation of the corneas entails exposing them to a medium of MEM. Prior to mounting the corneas, the antioxidant mixture will be added to the chemical to be tested or overlayed on the eye before addition of chemical or be added to the culture medium. The antioxidant can be incorporated into the ICE test method using the saline solution (OECD, 2018). The procedures are listed as follows:

1.4 Additions to Eggs for HET-CAM or CAMVA

To include the antioxidant mixture in egg-based assays, the mix can be added to the overlay or the test sample. After the exposure of the vessels of the membrane, the antioxidant mixture can be added to represent the mechanistic defenses in vivo that are not currently accounted for in egg-based assays (ICCVAM, 2010). The HET-CAM procedure is described by the ICCVAM-Recommended Test Method Protocol: Hen's Egg Test—Chorioallantoic Membrane (HET-CAM) Test Method (2010) (available at: https://ntp.niehs.nih.gov/iccvam/docs/protocols/ivocular-hetcam.pdf).

1) Add the antioxidant mixture to the surface of the membrane. Ensure the entirety of the membrane is covered in the antioxidant mixture. Leave the mixture on while applying the test substance.

2) Alternatively, add the antioxidant mixture to the chemical to be tested or the surface of the membrane. Start by preparing the antioxidant mixture and by adding the specific amount of antioxidant to a PBS solution and allow it to completely solubilize. For the best results, use a stir bar and a magnetic plate to slow stir until homogenous. If necessary, adjust the pH using Sodium hydroxide (NaOH, CASRN 1310-73-2) or Hydrochloric acid (HCl, CASRN 7647-01-0). Once the homogenous solution is obtained, proceed using this antioxidant mixture throughout the entirety of the assay. When applying the antioxidant mixture to the surface of the membrane, ensure the entirety of the membrane is covered 3) A prophetic analysis of styrene, a GHS NC and overpredicted FP by the HET-CAM test method, indicates that the HET-CAM score would fall below the irritant cut-off, resulting in a TN prediction of a GHS NC, with the use of the antioxidant mixture.

Depth of Injury (DOI) (Lebrun Labs LLC Procedure)

Only food source eyes are suitable for this procedure. Ensure proper documentation that the eyes are extra eyes from a food processing facility before placing the order. The day before the eyes arrive, place one bottle of antioxidant medium and one bottle of 1×PBS antioxidant buffer solution (Ascorbic Acid; 1.70 mM (0.3 mg/ml)) into the incubator and place one bottle of 1×PBS antioxidant buffer solution (Ascorbic Acid; 1.70 mM (0.3 mg/ml)) into the refrigerator.

Receiving the Eyes
1) Remove packing slip from the box and fill out the receiving form with the necessary information.
2) Retrieve a large Pyrex dish and place one ice pack in it.
3) Open the box and open the Styrofoam box that contain the eyes and take out the bag containing the eyes in jars. Remove the jars and immediately place on the ice packs in the large Pyrex dish prepared.

Eyelid Removal
1) Place a large piece of gauze on the plastic-lined pad in the work area.
2) Remove one eye from the jar and place on the gauze.
3) Use the scissors to make an incision behind the eyelids where it meets the sclera and cut until the whole eyelid is removed from the eyeball.
4) Use the scissors to cut the connective tissue, following the curved shape of the cornea but without touching it. Note: Do not remove too much connective tissue or it will be difficult to hold the eye when rinsing after dosing.
5) Place the eye in the "good" eye jar with refrigerated 1×PBS (Jar #1).
6) Continue until all eyes have the eyelids and connective tissue removed.
7) Place an eye holder in a small Pyrex dish.
8) Using a plastic pipette, fill the eye holder with Lissamine green dye.
9) Take the 18-gauge needle and syringe and remove the needle to aspirate the refrigerated 1×PBS.
10) Take an eye and dip the cornea into the Lissamine green dye in the eye holder and slowly move the eye around to ensure the cornea is completely covered.
11) Using the 18-gauge needle and syringe filled with the refrigerated 1×PBS, wash the Lissamine green dye off over the waste container.
12) Inspect the corneas for any Lissamine green dye indicating damage.
13) Place the undamaged eyes in a new jar (Jar #2) filled with fresh refrigerated 1×PBS and damaged eyes in a separate container to discard.

Preincubation
1) Open the 12 well plate(s) and fill each well with a "good" eye ensuring the cornea is facing up and the optic nerve is at the bottom of the well.
2) Add varying amounts of warm media from the incubator to each well ensuring the limbus is not covered. Note: The amount will vary per well due to inconsistent sizes of the eyes.
3) Put the lid onto the 12 well plate(s) and place into the incubator (37° C., 5% $CO_2$) for one hour.

Dosing
1) After incubation, remove the 12 well plate(s) from the incubator and place into the hood.
2) Label the wells on the lid with what is being tested.
3) Place an eye on the holder and carefully place a new cloning ring in the middle of the cornea without scratching it.
4) Fill the syringe with 40 mL of refrigerated 1×PBS antioxidant buffer solution (Ascorbic Acid; 1.70 mM (0.3 mg/ml)) by sucking it up from the beaker
5) Put the needle back on the syringe by twisting on, and then remove the cap that protects the needle.
6) Place the syringe flat on a sterile piece of foil.
7) Set the timer for "counting up".
8) Add by micropipette first 100 µL of antioxidant buffer solution (Ascorbic Acid; 1.70 mM (0.3 mg/ml)) then 100 µL of test substance
9) Start the timer for one minute.
10) After the one minute is over, remove the dosing ring and put in the proper container, and pick up the tissue without touching the cornea and hold it over the container for liquid waste.

Washing and Postincubation
1) Directly dispense 20 mL of antioxidant buffer solution (Ascorbic Acid; 1.70 mM (0.3 mg/ml)) onto the area of the cornea that was exposed to the sample as well as the back of the eyeball to ensure all the sample is washed off.
2) Place the eye back into its original well.
3) Continue for the rest of the eyes and samples.
4) Once all eyes are dosed, label a new 12 well plate and transfer the eyes into it.
5) Then add fresh media to the new 12 well plate(s).
6) Place the 12 well plate(s) into the incubator at 37° C.+5% $CO_2$ for 24 hours.

Cornea Extraction and Fixation
1) Retrieve the correct number of 12 well plate(s) and label the lid above each well with the correct dosing test substance.
2) Fill each well with 5 mL of the 4% paraformaldehyde
3) Once the 24-hour incubation is complete, remove the plate(s) from the incubator and place near cutting area.
4) Remove an eye and hold using the 2×2 gauze with the cornea facing up and ensuring the gauze does not cover the cornea or limbus.
5) Using the scalpel, poke a hole in the sclera about 2 mm from the cornea.
6) Using the scissors, cut along the edge of the cornea ensuring a 2 mm border of sclera.
7) Make sure the cuts are smooth and ensure the cornea does not come into contact with the scissors or the cut mat.
8) Once the cornea is separated from the rest of the eye, place the cornea with the iris attached directly into the paraformaldehyde and slowly move back and forth to get rid of any folding.
9) Continue until all corneas have been removed.
10) Saran Wrap the plate and then put the lid on
11) Put the plate(s) in the fridge.

Sucrose Infiltration
1) Label a new 12 well plate.
2) Remove the plate(s) with the corneas suspended in 4% paraformaldehyde from the fridge.
3) Place a cutting mat on the bench and a large gauze pad down.
4) Remove each cornea one by one and use the small forceps to remove the iris.
5) Cut the cornea in half.
6) Once the cornea is cut in half, place the cornea back into the correct well of paraformaldehyde.
7) Get a new 12 well plate and fill each well with 5 mL of 10% sucrose solution.
8) Transfer the corneas from the 4% paraformaldehyde solution into the new 12 well plate containing the 10% sucrose.
9) Let sit for 15 minutes.
10) During the 15 minutes, prepare the 2:1 10% sucrose: 30% sucrose solution in a 50 mL conical tube.
11) Once the 15 minutes is done, use a serological pipette to remove the 10% sucrose from the wells.

12) Fill the same wells with 4.5 mL of the 2:1 10% sucrose:30% sucrose solution.
13) Let sit for 15 minutes.
14) During the 15 minutes, prepare the 1:1 10% sucrose:30% sucrose solution.
15) Once the 15 minutes is done, use a serological pipette to remove the 2:1 10% sucrose:30% sucrose solution from the wells.
16) Fill the same wells with 5 mL of the 1:1 10% sucrose:30% sucrose solution.
17) Let sit for 15 minutes.
18) During the 15 minutes, prepare the 1:2 10% sucrose:30% sucrose solution.
19) Once the 15 minutes is done, use a serological pipette to remove the 1:1 10% sucrose:30% sucrose solution from the wells.
20) Fill the same wells with 4.5 mL of the 1:2 10% sucrose:30% sucrose solution.
21) Let sit for 15 minutes.
22) Once the 15 minutes is done, remove the 1:2 10% sucrose:30% sucrose solution from the wells.
23) Fill the same wells with 5 mL of 30% sucrose (#1).
24) Let sit for 15 minutes.
25) Once the 15 minutes is done remove the 30% sucrose solution and replace it with another 5 mL of 30% sucrose solution (#2).
26) Let sit for 15 minutes.
27) Once the 15 minutes is done remove the 30% sucrose solution and replace it with another 5 mL of 30% sucrose solution (#3).
28) Let sit for 15 minutes.

OCT Embedding and Liquid Nitrogen Freezing
1) Label all pink bags with your name, date, sample name, and Lot #.
2) Label 1 large white bag with name, date, samples and # of each, and Lot #.
3) Take out the correct number of Tissue-Tek cryomolds, and forceps.
4) Fill the first square of the Tissue-Tek cryomold with OCT.
5) Grab the outer round edge of the cornea with the forceps and place the straight edge into the OCT so it lays along the bottom of the cryomold.
6) Ensure the cornea is completely vertical and not bent.
7) Inspect from above and the sides to ensure it is in the correct orientation.
8) Rest the cryomold on the coat hanger holder and slowly insert the cryomold into the Dewar Flask until only the bottom of the cryomold is exposed to the liquid nitrogen.
9) DO NOT LET THE LIQUID NITROGEN TOUCH THE OCT DIRECTLY.
10) Once the bottom of the cryomold is in the liquid nitrogen, you should be able to see the OCT from above go from clear to completely white.
11) Once the OCT above the liquid nitrogen is completely white and frozen and has no air bubbles, the entire cryomold can be submerged into the liquid nitrogen and kept there for 20 seconds to ensure adequate freezing.
12) After the 20 seconds is finished, use the coat hanger mold to remove the cryomold and ensure all excess liquid nitrogen is poured into the Dewar Flask.
13) The entire mold can then be placed in a Pyrex dish for a couple of seconds.
14) Immediately transfer the entire cryomold with the frozen cornea in it, to its respective labeled pink bag.
15) Immediately place the pink bag into the large white bag in the −80° C. freezer for storage.

Cryosectioning
1) Lay out paper towel to put the slides on.
2) Label the slides using the following labeling system:
3) Once all slides are labelled, lay them out on the paper towel in an organized manner.
4) Turn the light on in the cryostat.
5) Ensure the cryostat is at −25° C.
6) Ensure the small chuck is in the cryostat and in the proper freezing area on the left.
7) Ensure the 1 g metal weight is in the cryostat and at the correct temperature (if not in the cryostat, place the weight in the cryostat and wait for it to cool down to the −25° C. temperature).
8) Put the desired paint brush in the cryostat to make sure it gets to the proper temperature.
9) Retrieve a bottle of OCT if not on top of the cryostat already.
10) Check the micron setting to make sure it is set to the correct micron value.
11) Retrieve the first sample from the −80° C. freezer.
12) Take the frozen sample (still in the Tissue-Tek cryomold) and remove it from the pink bag.
13) Place the pink bag in the cryostat and the sample on top of the pink bag.
14) Close the cryostat lid and leave the sample until it is able to be popped out of the mold with ease (approximately 5-8 minutes).
15) When the sample is ready to be popped out, flip the mold upside down so when the sample is popped out it will land directly on the pink bag. The top of the frozen sample (the part exposed to air while in the mold) should be touching the pink bag. The bottom of the frozen sample (the part touching the inside of the mold which has the flat side of the cornea) should be facing upwards so you can slightly see the outline of the sample.
16) Once the sample is popped out of the mold, leave it in the orientation.
17) Get the OCT and squeeze it onto the chuck, starting from the center and dispensing in a circular motion following the rings on the chuck until the entire chuck has a layer of OCT on it.
18) Quickly pick up the frozen sample and place it on the OCT.
19) Get the 1 g metal weight and carefully place it on top of the frozen sample so it adheres to the OCT and freezes completely horizontal and flat to allow for proper cutting.
20) Close the lid and wait for the OCT to completely freeze and bond to the frozen sample (approximately 5 minutes).
21) Once the OCT is completely frozen and the sample is ready to be cut, open the lid and remove the 1 g weight.
22) Lift the chuck up and insert it into the block and tighten to secure it.
23) Use the buttons on the left-hand side to adjust the distance of the sample from the blade.
24) Once the sample is in the correct position/distance from the blade, slowly turn the handle to see if further adjustment is needed.
25) In the beginning, only certain parts of the sample may be getting cut (like the middle, bottom, or edge)—this is normal.
26) Continue slowly turning the handle to trim the frozen sample and eventually trim to the point where the entire frozen sample is being cut evenly. As sections (full or partial) are being cut, lift the glass and use the paint brush to wipe away the excess to have a clean slate for future sections.

27) Once the sections being cut are full squares and the entire cornea is being included in a section, it is ready to be put on slides.
28) Use the paint brush to wipe away any sections and start with a clean area.
29) Turn the handle to get a clean full section.
30) Lift the glass to expose the section. If the section is slightly curled or scrunched, use the paint brush to straighten it out by lightly putting the edge of the bristles on the bottom part of the section and gently pulling towards yourself to remove the wrinkles.
31) Get the slide and flip it over so the part where the section sticks is facing down.
32) Hover the slide over the section in the exact spot it will be placed on the slide.
33) Slowly put the bottom edge of the slide (closest to you) on the bottom of the section and quickly roll the slide towards the top of the slide (closest to the blade) to ensure the section gets placed on the slide without air bubbles or folds.
34) Once the section is attached to the slide, flip it over so the side that the section is on is faced up.
35) Place the slide back on the paper towel.
36) Put the glass back down gently so you can continue cutting more sections.
37) Continue cutting sections one by one and adding them to each slide closest to the plus signs.
38) Once all slides of the sample have 1 section on it, trim the sections about 100 microns by turning the handle 15 times.
39) Use the paint brush to wipe away the sections and provide a clean area.
40) Cut sections one by one again and add them to the middle of the slide until each slide for the sample has a middle section on it.
41) Trim the section again by 100 microns and use the paint brush to wipe away the sections.
42) Cut sections one by one again and add them to the top of the slide until each slide for the sample has a top section on it. Each slide should have 3 sections on it now.
43) Once all slides have 3 sections on them the cutting is done.
44) Remove the chuck from the block and leave it outside of the cryostat (approximately 1 minute) to slightly thaw the sample so it can be removed from the chuck.
45) Once the sample has been slightly thawed, remove it from the chuck and place it back into the pink bag and then the −80° C.
46) Either stain the slides in the same day, or sore the slides in a slide box. Slide box must be properly labeled using labeling tape regardless of same day staining or not.

Staining
1) Lay out the slides, face up, in the slide box.
2) So that the top and bottom edge (white writing part and plus sign part) are laying on the groove where the slides would be put into.
3) If the slides came from the fridge, let them get to room temperature (approximately 10 minutes).
4) Put the Phalloidin and DAPI stock solution tubes on the cooling rack and keep them covered with foil to protect them from light.
5) Prepare the phalloidin mixture (this is enough to cover 16 sections). Dispense 800 μL of 1×PBS into the microcentrifuge tube. Dispense 20 μL of phalloidin into the 1×PBS. Invert to mix and place the conical tube in the cooling rack (covered with foil) until ready to dispense the solution on the sections. Phalloidin is light sensitive so keep covered at all times.
6) Dispense 50 μL on each individual cornea section.
7) Once all sections are covered with the Phalloidin solution, close the lid of the slide box but do not completely close it—just let the lid lay closed.
8) Get the foil and cover the slide box to prevent any light from going through.
9) Turn off the lights in the room to help with light issues.
10) Let the solution sit for 20 minutes.
11) Once the 20 minutes is done, remove the foil and open the lid.
12) Take each slide one by one and dump the phalloidin liquid in the waste beaker.
13) Once the excess phalloidin has been removed, use a disposable pipette to rinse the slide off with 1×PBS. Dispense the 1×PBS at the top of the slide and let the PBS run down the slide to rinse it. DO NOT dispense the PBS directly on the sections or they could come off or get ruined.
14) Once all slides have been rinsed, lay them back in the slide box and lay the lid closed so the DAPI solution can be made.
15) Prepare the DAPI mixture (this is enough to fill 1 conical tube that holds 5 slides). Fill the 50 mL conical tube with 50 mL of 1×PBS. Dispense 10 uL of DAPI into the conical tube. Put the lid on and shake until it is all incorporated. DAPI is light sensitive so keep covered at all times.
16) Pour the DAPI solution into the Coplin jar and transfer the slides into the jar.
17) Cover the Coplin jar with foil and turn the lights off once again.
18) Keep the slides in the solution for 5 minutes.
19) Once the 5 minutes is up, take the slides out one by one and use a disposable pipette to rinse off the excess DAPI solution with 1×PBS.
20) Once the slides have been rinsed off, place them lying flat in the slide box once again.

Cover Slip Addition
1) Place 2 stacked Whatman paper on the table and keep another single paper on the side out of the way.
2) Dispense about 3 drops of glycerol on each individual cornea section.
3) Slowly place a cover slip onto the slide starting from one end and slowly angling the cover slip even more until the entire thing is on the slide. Dropping the cover slip fast will cause the formation of air bubbles and may ruin the section due to potential movement.
4) Once the cover slip is completely on, pick up the slide and place the side on its side at about a 45-degree angle on the paper (slide is facing the paper and the cover slip side is facing towards you).
5) Slowly increase the angle of the slide by bringing the top side towards you until it makes a 90-degree angle with the Whatman paper.
6) This will make a seal between the Whatman paper and the slide and cause the excess 50% glycerol to be absorbed by the Whatman paper.
7) Once the excess 50% glycerol is removed, flip the slides over to the other side and hold it against the Whatman paper at a 90-degree angle to remove any excess 50% glycerol from that end.

8) Lay the slide on the slide box again face up and use the Whatman paper left on the side to absorb any excess 50% glycerol at the edges by carefully holding the edge of the paper to the edge of the coverslip on the slide.
9) Once all of the excess 50% glycerol has been removed, the slides are ready for imaging.
10) Keep them in the slide box with the lid closed to prevent unnecessary light exposure.

Imaging

1) Turn on the microscope (black switch on the right side).
2) At the base of the microscope the word "set" will show up in red indicating the microscope is on.
3) Turn on the fluorescence light on the power box to the left of the microscope.
4) Give the light about 3 minutes to warm up.
5) While the light is warming up, click on the "DoI Images" folder on the desktop.
6) Create a new folder within labeled "Experiment dd-mm-yy Intact Cornea 24 hour Series"
7) Within that folder, make a folder for each sample that was tested.
8) Within the folder for each sample make two folders each labeled "100×" and "400×"
9) Open the Thor Camera software and click the down arrow on the left of the screen that pops up.
10) Click "CS235MU"
11) Once the imaging window comes up, maximize the screen.
12) Put a slide in the microscope and align the 10× lens.
13) Under the eye piece there is a silver disc embedded into the microscope that can rotate to change the fluorescence filters (4 settings labeled—1, 2, 3, & 4). 3—FITC—DAPI
14) Rotate the disc to filter 3 and look through the eye piece—the cornea should be illuminated green with the epi being brighter green than the stroma. This means the phalloidin stained the cornea adequately.
15) Rotate the disc to filter 4 and look through the eye piece—the cornea should be illuminated blue with the nuclei in the epi a defined blue. This means the DAPI stained the cornea adequately.
16) Now that the stain has been checked it is ready to be imaged.
17) Keep the disc that controls the filter at number.
18) Starting with DAPI makes it easier and faster to focus the image.
19) Ensure the 10× lens is being used.
20) While looking through the eye piece, position the cornea where you want capture the image making sure to include the epithelium, stroma, and endothelium. The cornea must be centered in the screen and completely straight. Horizontal or vertical depending on the orientation of the camera.
21) Once the cornea is set up in the correct position, pull out the metal bar out to the left of the eyepiece on the side of the microscope. Below the bar it will say "photo, photo/vis, vis" This will allow the camera to see the image instead of you through the eye piece.
22) At the top bar, click the icon that looks like 3 gears (settings button). Move the settings window to the very right so it does not block the screen where the image will be displayed.
23) Set the exposure time to 250 ms and then press enter.
24) In the top left corner click the round green button with the white triangle in it. "Live image"
25) Once the image is displayed on the screen, adjust it up/down left/right to make it centered on the screen.
26) If the image needs to be slightly rotated to make it horizontal, slowly rotate the stage.
27) Once the image in centered and positioned correctly, use the fine tune knob to focus the image until it is clear.
28) Once the image is clear, determine if the exposure time is high enough or if it needs to be adjusted. For DAPI, the nuclei should be visible and defined but not extremely bright.
29) Once the exposure is adjusted to the correct level, press the live image button once again so it stops showing the live image. The button should be a green circle with a white square in it.
30) Then press the camera icon to take a picture.
31) The camera icon and the icons near it will grey out for a little bit and then the color will come back.
32) Once the color comes back to the icons, the picture is done being taken and ready to save.
33) To save the image, press the floppy disk with the tree in the bottom right.
34) It will bring up the file explorer where you find the folder you made earlier and save it under the correct sample name. This will be saved under the 100× folder.
35) The picture will be labeled: "'sample name' 'slide #' 'section letter' 100×'DAPI or FITC'" Ex. "Water 1A 100×DAPI"
36) Once the DAPI image is saved under the 100× folder, the phalloidin image is ready to be taken.
37) DO NOT MOVE THE STAGE.
38) ONLY turn the disc to change the filter from number 4 to number 3 so the phalloidin stain can be seen.
39) Once the filter is on number 3, click the settings button once again.
40) Start off by changing the exposure to approximately 5000.
41) Click the live image button and see how bright the phalloidin stain is.
42) The goal is to have the stroma bright and clearly visible. If the epi will become over exposed if done correctly and that is acceptable.
43) Continue to adjust the exposure until the stroma is very bright and clear.
44) Once the exposure is adjusted and the image is focused, stop the live image display.
45) Click the camera icon and wait for the image to be taken.
46) Save the image in the same folder and label it correctly (in this case it will be the same label as the previous picture but will have "DAPI" switched out for "FITC"): "'sample name' slide #'section letter' 100× 'DAPI or FITC'" Ex. "Water 1A 100×FITC"
47) Continue taking pictures for the rest of the sections on the slide until all 100× images are complete. Between each section, push the rod in so you can see the sections through the eye piece. When ready to image, pull the rod out again so the camera can capture the image.
48) Turn the lens to the 40× lens.
49) Turn the disc so the filter is on number 4 (DAPI).
50) Push the rod in so you can visualize the sections through the eye piece.
51) Position the light over the first section and find a straight clear section of the epithelium.
52) Pull the rod out.
53) Set the exposure to 150 ms and press enter.

54) Press the live image button and see if the image is at the correct exposure. The nuclei should not be too dark or too bright.
55) Once the image has the correct exposure and is focused, stop the live image. 56) Press the camera icon and wait for the image to be taken.
57) Press the save image button and save the image under the correct sample name and in the 400× folder.
58) Label it correctly: "'sample name' 'slide #' 'section letter' 400×'DAPI or FITC'" Ex. "Water 1A 400× DAPI"
59) Once the DAPI image is saved under the 400× folder, the phalloidin image is ready to be taken.
60) Do not move the stage.
61) Only turn the disc to change the filter from number 4 to number 3 so the phalloidin stain can be seen.
62) Once the filter is on number 3, click the settings button once again.
63) Start off by changing the exposure to approximately 2000.
64) Click the live image button and see how bright the phalloidin stain is.
65) The epithelium should be illuminated but not over exposed. It should be clear and defined.
66) Once the exposure is adjusted and the image is focused, stop the live image.
67) Press the camera icon and wait for the image to be taken.
68) Save the image in the same folder and label it correctly (in this case it will be the same label as the previous picture but will have "DAPI" switched out for "FITC"): "'sample name' 'slide #' 'section letter' 400× 'DAPI or FITC'". Ex. "Water 1A 400×FITC".
69) Continue taking pictures for the rest of the sections on the slide until all 400× images are complete. Between each section, push the rod in so you can see the sections through the eye piece. When ready to image, pull the rod out again so the camera can capture the image.

The results shown in Table 12 indicate that the false positive rate is significantly reduced by the presence of antioxidant formulation for the DoI procedure compared with other test methods.

Legend: GHS=Globally Harmonized System of classification and labeling of chemicals; NC=Nonclassified; BCOP (LLBO)/(OP-KIT)=Bovine Corneal Opacity & Permeability Laser Light-Based Opacitometer/Opacitometer Kit; EPI=EpiOcular; OI=Ocular Irritection; DoI=Depth of Injury; CNM=Criteria not met; FP=False positive; TN=True negative.

While various aspects and embodiments have been disclosed herein, other aspects and embodiments will be apparent to those skilled in the art.

The various aspects and embodiments disclosed herein are for purposes of illustration and are not intended to be limiting, with the true scope and spirit being indicated by the following claims.

One skilled in the art will appreciate that this and other processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

BIBLIOGRAPHY

Adedara I A., Farombi E O. (2014). "Kolaviron protects against ethylene glycol monoethyl ether-induced toxicity in boar spermatozoa". Andrologia. 46(4):399-407. doi: 10.1111/and.12095.

Babizhayev M A. (2016). "Generation of reactive oxygen species in the anterior eye segment. Synergistic codrugs of N-acetylcarnosine lubricant eye drops and mitochondria-targeted antioxidant act as a powerful therapeutic platform for the treatment of cataracts and primary open-angle glaucoma". BBA Clin. 6:49-68. doi: 10.1016/j.bbacli.2016.04.004.

Behndig A., Svensson B., Marklund S L., Karlsson K. (1998). "Superoxide dismutase isoenzymes in the human eye". Invest Ophthalmol Vis Sci. 39(3):471-5.

Belvedere G., Tursi F. (1981). "Styrene oxidation to styrene oxide in human blood erythrocytes and lymphocytes".

TABLE 12

| Chemical Name | CASRN | in vivo GHS | BCOP (LLBO) | BCOP (OP-KIT) | EPI | OI | DoI |
|---|---|---|---|---|---|---|---|
| Sodium lauryl sulfate (3%) | 151-21-3 | NC | FP | FP | FP | FP | TN |
| Ethyl acetate | 141-78-6 | NC | | FP | FP | FP | FP |
| Cyclohexanone | 108-94-1 | NC | | FP | FP | | FP |
| 2-(2-Ethoxyethoxy) ethanol | 111-90-0 | NC | | | FP | FP | TN |
| 3-Phenoxy benzyl alcohol | 13826-35-2 | NC | | | FP | FP | FP |
| 2-Ethoxyethyl methacrylate | 2370-63-0 | NC | | | FP | FP | TN |
| 2,4-Pentanedione | 123-54-6 | NC | | FP | FP | | FP |
| 1-Nitropropane | 108-03-2 | NC | FP | FP | | | TN |
| Ethylene glycol diethyl ether | 629-14-1 | NC | | | FP | FP | FP |
| Styrene | 100-42-5 | NC | | | FP | TN | FP |
| 1,9-Decadiene | 1647-16-1 | NC | FP | | TN | TN | TN |
| p-Methyl thiobenzaldehyde | 3446-89-7 | NC | | | TN | | TN |
| 2,2-Dimethyl-3-pentanol | 3970-62-5 | NC | | | FP | FP | FP |
| 1,3-Di-iso-propylbenzene | 99-62-7 | NC | FP | | TN | FP | TN |
| Triphenyl phosphite | 101-02-0 | NC | | | FP | | TN |
| Triethylene glycol | 112-27-6 | NC | | | FP | | TN |
| | | | 0 TN | 0 TN | 3 TN | 2 TN | 9 TN |
| | | | 4 FP | 5 FP | 12 FP | 8 FP | 7 FP |
| | | FPR | 100% (4/4) | 100% (5/5) | 80% (12/15) | 80% (8/10) | 43.8% (7/16) |

Research Communications in Chemical Pathology and Pharmacology. 33(2):273-282.

Bodin A., Linnerbord M., Nilsson J L G., Karlberg A T. (2003). "Structure elucidation, synthesis, and contact allergen activity of a major hydroperoxide formed at autoxidation of the ethoxylated surfactant C12E5". Chem Res Toxicol. 16(5):575-82. doi:10.1021/tx025609n Cabrera M P., Chihuailaf R H. (2011). "Antioxidants and the integrity of ocular tissues". Vet Med Int. 905153. doi: 10.4061/2011/905153.

Carlson G P., Turner M., Mantick N A. (2006). "Effects of styrene and styrene oxide on glutathione-related antioxidant enzymes". Toxicology. October 29; 227(3):217-26. doi: 10.1016/j.tox.2006.08.006.

Carr A C., Maggini S. (2017). "Vitamin C and Immune Function". Nutrients. 9(11):1211. doi: 10.3390/nu9111211

Chen C., Jiang X. (2019). "Transport property prediction and inhomogeneity analysis of supercritical n-Dodecane by molecular dynamics simulation". Fuel. 244:48-60. doi: 10.1016/j.fuel.2019.01.181.

Chen Y., Mehta G., Vasiliou V. (2009). "Antioxidant defenses in the ocular surface". Ocul Surf. 7(4):176-185. doi:10.1016/s1542-0124(12)70185-4.

Chirila T V., Walker L N., Constable I J., Thompson D E., Barrett G D. (1991). "Cytotoxic effects of residual chemicals from polymeric biomaterials for artificial soft intraocular lenses". J Cataract Refract Surg.17(2):154-62. doi: 10.1016/s0886-3350(13)80245-3

Choksi N., Lebrun S., Nguyen M., Daniel A., DeGeorge G., Willoughby J., Layton A., Lowther D., Merrill J., Matheson J., Barroso K., Yozzo K., Casey W., Allen D. (2020). "Validation of the OptiSafe™ eye irritation test". Cutan Ocul Toxicol. 39(3):180-192. doi:10.1080/15569527.2020.1787431.

Clark D E. (2001). "Peroxides and peroxide-forming compounds". Chem. Health Saf. 8(5):12-22. doi: 10.1021/acs.chas.8b08507.

Conrady C D., Joos Z P., Patel B C. (2016). "Review: The Lacrimal Gland and Its Role in Dry Eye". Journal of ophthalmology. 7542929. doi: 10.1155/2016/7542929.

de Berardinis E., Tieri O., Polzella A., luglio N. (1965). "The chemical composition of the human aqueous humour in normal and pathological conditions". Experimental Eye Research. 4(3):179-186. doi: 10.1016/S0014-4835(65)80030-6.

Di Tommaso S., Rotureau P., Crescenzi O., Adamo C. (2011). "Oxidation mechanism of diethyl ether: a complex process for a simple molecule". Physical Chemistry Chemical Physics. 13:14636-14645. doi: 10.1039/C1CP21357A.

Draize J H., Woodard G., Calvery H O. (1944). "Methods for the study of irritation and toxicity of substances applied topically to the skin and mucous membranes". J. Pharmacol. And Exp. Therapeutics. 82: 377-390.

Dwarakanath V., Pope G A. (1998). "New Approach for Estimating Alcohol Partition Coefficients between Nonaqueous Phase Liquids and Water". Environ. Sci. Technol. 32(11):1662-1666. doi: 10.1021/es9707441

EC. (2001). Commission Directive 2001/59/EC of 6 Aug. 2001 adapting to technical progress for the 28th time Council Directive 67/548/EEC on the approximation of the laws, regulations and administrative provisions relating to the classification, packaging and labelling of dangerous substances. Official Journal of the European Communities L225, 1-333.

EC. (2008a). Classification, Regulation and Packaging (CLP): Regulation (EC) No. 1272/2008. Available: [http://echa.europa.eu/web/guest/regulations/clp].

EC. (2008b). Regulation (EC) No 1272/2008 of the European Parliament and of the Council of 16 Dec. 2008 on Classification, Labelling and Packaging of substances and mixtures, amending and repealing Directives 67/548/EEC and 1999/45/EC, and amending Regulation (EC) No 1907/2006. Official Journal of the European Union L353, 1-1355.

Faraguna F., Siuc V., Vidović E., Jukic A. (2015). "Reactivity ratios and properties of copolymers of 2-ethoxyethyl methacrylate with dodecyl methacrylate or styrene". J Polym Res. 22(245). doi:10.1007/s10965-015-0890-4.

Fisher W B., VanPeppen J F. (2000). "Cyclohexanol and Cyclohexanone". Kirk-Othmer Encyclopedia of Chemical Technology. doi: 10.1002/0471238961.0325031206091908.a01.

Frater R. (2009). "Neutralization of Acid in Glycol Methacrylate and the Use of Cyclohexanol as a Plasticizer". Stain Technology. 56(2):99-101. doi: 10.3109/10520298109067290.

Garcia F., Garcia J M., Rubio F., de la Pena J L., Guzman J., Riande E. (2002). "Reaction kinetics and gel effect on the polymerization of 2-ethoxyethyl methacrylate and 2(2-ethoxyethoxy) ethyl methacrylate". Journal of Polymer Science Part A: Polymer Chemistry. 40(22). doi:10.1002/pola.10480

Gierke J S., Sanders D L., Perram D L. (1999). "Laboratory Studies of Aqueous Partitioning Tracer Tests for Measuring Nonaqueous Phase Liquid Volumes". Water Environment Research. 71(4). doi: 10.2175/106143097X122202.

Grobe G M., Reichl S. (2013). "Characterization of vitamin C-induced cell sheets formed from primary and immortalized human corneal stromal cells for tissue engineering applications". Cells Tissues Organs. 197(4):283-97. doi: 10.1159/000346172.

Gulcin İ. (2020). "Antioxidants and antioxidant methods: an updated overview". Arch Toxicol. 94(3):651-715. doi: 10.1007/s00204-020-02689-3.

Han Z., Zhang Z., Guan Y., Chen B., Yu M., Zhang L., Fang J., Gao Y., Guo Z. (2021). "New insights into Vitamin C function: Vitamin C induces JAK2 activation through its receptor-like transporter SVCT2". Int J Biol Macromol. 15; 173:379-398. doi: 10.1016/j.ijbiomac.2021.01.120.

H.R.4148. (2014). Humane Cosmetics Act 113th Congress (2013-2014). Rep. Moran, James P. [D-VA-8] (Introduced Mar. 5, 2014). https://beta.congress.gov/bill/113th-congress/house-bill/4148/

Huber M L., Laesecke A., Perkins R. (2004). "Transport Properties of n-Dodecane". Energy Fuels. 18(4):968-975. doi: 10.1021/ef034109e.

Humane Society. (2017). Timeline: Cosmetics Testing on Animals: The Humane Society of the United States. [online] Available at: http://www.humanesociety.org/issues/cosmetic_testing/timelines/timeline-cosmetics-testing-on-animals.html [Accessed 27 Dec. 2017].

ICCVAM. (2009). Independent Scientific Peer Review Panel Report: Evaluation of the Validation Status of Alternative Ocular Safety Testing Methods and Approaches. Available at: http://iccvam.niehs.nih.gov/docs/ocutox_docs/OcularPRPRept2009.pdf ICCVAM. (2010). "ICCVAM-Recommended Test Method Protocol: Hen's Egg Test—Chorioallantoic Membrane (HET-CAM) Test Method". Available at: https://ntp.niehs.nih.gov/iccvam/docs/protocols/ivocular-het-cam.pdf ICCVAM-NICEATM. (2013). "Short Time Exposure (STE) Test Method Summary Review Document", National Toxicology Program. Available at: http://www.ntp.niehs.nih.gov/iccvam/docs/ocutox_docs/STE-SRD-NICEATM-508.pdf.

Jomova K., Valko M. (2011). "Advances in metal-induced oxidative stress and human disease". Toxicology. 283(2-3):65-87. doi: 10.1016/j.tox.2011.03.001.

Kanter J. (2017). E. U. Bans Cosmetics With Animal-Tested Ingredients. [online] Nytimes.com. Available at: http://www.nytimes.com/2013/03/11/business/global/eu-to-ban-cosmetics-with-animal-tested-ingredients.html [Accessed 31 Dec. 2017].

Kay J H., Calandra J C. (1962). "Interpretation of eye irritation tests". J. Soc. Cosmet. Chem. 13: 281-289.

Kim Y H., Graham A D., Li W., Radke C J., Lin M C. (2019). "Human lacrimal production rate and wetted length of modified Schirmer's tear test strips". Trans Vis Sci Tech. 8(3):40.

Kovacs E., Wolkober Z. (1973). "Effectivity of organic phosphites". Journal of Polymer Science: Polymer Symposia. 40(1):73-78. doi: 10.1002/polc.5070400110.

Lebrun S., Choksi N., Daniel A., Allen D., Casey W. (2019). "Prevalidation of the OptiSafe Ocular Irritation Assay for the Detection of Ocular Corrosives". SOT 2020 Annual Meeting.

Lebrun S., Nguyen L., Chavez S., Chan R., Le D., Nguyen M., Jester J V. (2020). "Same-chemical comparison of nonanimal eye irritation test methods: Bovine corneal permeability, EpiOcular™, isolated chicken eye, ocular Irritection®, OptiSafe™, and short time exposure". Toxicol In Vitro. 2020: 105070. doi: 10.1016/j.tiv.2020.105070.

Levene C I., Bates C J. (1975). "Ascorbic acid and collagen synthesis in cultured fibroblasts". Ann NY Acad Sci. 258:288-306. doi: 10.1111/j.1749-6632.1975.tb29289.x.

Liu R., Mabury S A. (2019). "Organophosphite Antioxidants in Indoor Dust Represent an Indirect Source of Organophosphate Esters". Environ Sci Technol. 53(4):1805-1811. doi: 10.1021/acs.est.8b05545.

MatTek Corporation. (2021). Protocol: "EpiOcular™ Eye Irritation Test (OCL-200-EIT) For the prediction of acute ocular irritation of chemicals: Identification of chemicals not requiring classification and labeling for eye irritation or serious eye damage". Available at: https://www.mattek.com/wp-content/uploads/OCL-200-EIT-Eye-Irritation-Test-Protocol-MK-24-007-0055_02_02_2021.pdf Medscape. (2017). "Vitamin C (Ascorbic Acid)". Available at: https://emedicine.medscape.com/article/2088649-overview Mikulás K., Hermann P., Gera I., Komlódi T., Horváth G., Ambrus A., Tretter L. (2018). "Triethylene glycol dimethacrylate impairs bioenergetic functions and induces oxidative stress in mitochondria via inhibiting respiratory Complex I". Dent Mater. 34(7):e166-e181. doi: 10.1016/j.dental.2018.03.012

Mottley C., Robinson R E., Mason R P. (1991). "Free radical formation in the oxidation of malondialdehyde and acetylacetone by peroxidase enzymes". Archives of Biochemistry and Biophysics. 289(1):153-160. doi: 10.1016/0003-9861(91)90455-R.

Nakchat O., Nalinratana N., Meksuriyen D., Pongsamart S. (2014). "Tamarind seed coat extract restores reactive oxygen species through attenuation of glutathione level and antioxidant enzyme expression in human skin fibroblasts in response to oxidative stress". Asian Pac J Trop Biomed. 4(5):379-385. doi:10.12980/APJTB.4.2014C806.

Niaz K., Mabqool F., Khan F., Hassan F I., Baeeri M., Navaei-Nigjeh M., Hassani S., Gholami M., Abdollahi M. (2017). "Molecular mechanisms of action of styrene toxicity in blood plasma and liver". Environmental Toxicology. 32:2256-2266. doi: 10.1002/tox.22441

Nita M., Grzybowski A. (2016). "The Role of the Reactive Oxygen Species and Oxidative Stress in the Pathomechanism of the Age-Related Ocular Diseases and Other Pathologies of the Anterior and Posterior Eye Segments in Adults". Oxid Med Cell Longev. 2016:3164734. doi: 10.1155/2016/3164734.

Njie-Mbye Y F., Kulkarni-Chitnis M., Opere C A., Barrett A., Ohia S E. (2013). "Lipid peroxidation: pathophysiological and pharmacological implications in the eye". Front Physiol. 4:366. doi:10.3389/fphys.2013.00366.

OECD. (2018). "Test No. 438: Isolated Chicken Eye Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, https://doi.org/10.1787/9789264203860-en.

OECD. (2019a). "Test No. 492: Reconstructed human Cornea-like Epithelium (RhCE) test method for identifying chemicals not requiring classification and labelling for eye irritation or serious eye damage". OECD Guidelines for the Testing of Chemicals, Section 4, OECD Publishing, Paris, https://doi.org/10.1787/9789264242548-en.

OECD. (2019b). "Test No. 496: in vitro Macromolecular Test Method for Identifying Chemicals Inducing Serious Eye Damage and Chemicals not Requiring Classification for Eye Irritation or Serious Eye Damage. OECD Guidelines for the Testing of Chemicals, Section 4, OECD Publishing, Paris, https://doi.org/10.1787/970e5cd9-en OECD. (2020a). "Test No. 437: Bovine Corneal Opacity and Permeability Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, https://doi.org/10.1787/9789264203846-en OECD. (2020b). "Test No. 491: Short Time Exposure In Vitro Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, https://doi.org/10.1787/9789264242432-en.

Palmlof M., Hjertbeg T. (2000). "Chemical and mechanical changes in poly(ethylene-co-1,9-decadiene) following crosslinking induced by peroxides". Polymer. 41(17): 6497-6505. doi: 10.1016/S0032-3861(99)00881-2.

Paterson C A., O'Rourke M. (1987). "Vitamin C Levels in Human Tears". Arch Opthalmol. 105(3): 376-377. doi: 10.1001/archopht.1987.01060030096034.

Peterkofsky B. (1972). "The effect of ascorbic acid on collagen polypeptide synthesis and proline hydroxylation during the growth of cultured fibroblasts". Arch Biochem Biophys. 152(1):318-28. doi: 10.1016/0003-9861(72)90221-4.

Rodrigues A P., da Fonseca L M., de Faria Oliveira O M., Brunetti I L., Ximenes V F. (2006). "Oxidation of acetylacetone catalyzed by horseradish peroxidase in the absence of hydrogen peroxide". Biochim Biophys Acta.

1760(12):1755-61. doi: 10.1016/j.bbagen.2006.09.008.

S.697. (2016). Frank R. Lautenberg Chemical Safety for the 21st Century Act. 114th Congress (2015-2016) https://www.congress.gov/bill/114th-congress/senate-bill/697.

Schwetlick K., Pionteck T J., Habicher W D. (1987). "Organophosphorus antioxidants—VIII. Kinetics and mechanism of the reaction of organic phosphites with peroxy radicals". European Polymer Journal. 23(5): 383-388. doi: 10.1016/0014-3057(87)90167-4.

Schwetlick K., Habicher W D. (1995). "Organophosphorus antioxidants action mechanisms and new trends". Die Angewandte Makromolekular Chemie. 232(1): 239-246. doi: 10.1002/apmc.1995.052320115.

Senate Joint Resolution 22. (2014). Introduced by Senator Block. Mar. 24, 2014. http://leginfo.legislature.ca.gov/faces/billNavClient.xhtml?bill_id=201320140SJR22&search_keywords Smedberg A., Hjertberg T., Gustafsson B. (1997). "Cross-linking reactions in an unsaturated low density polyethylene". Polymer. 38(16):4127-4138. doi: 10.1016/S0032-3861(96)00994-9.

Su L J., Zhang J H., Gomez H., Murugan R., Hong X., Xu D., Jiang F., Peng Z Y. (2019). "Reactive Oxygen Species-Induced Lipid Peroxidation in Apoptosis, Autophagy, and Ferroptosis". Oxid Med Cell Longev. 2019:5080843. doi: 10.1155/2019/5080843.

Suksomtip M., Ukrisdawithid S., Bhusawang P., Pongsamart S. (2010). "Phenolic compound content, antioxidant and radical-scavenging properties of methanolic extracts from the seed coat of certain thai tamarind culivars". Journal of Food Biochemistry. 34(5). doi: 10.1111/j.1745-4514.2009.00323.x.

Tei T., Sato Y., Hagiya K., Tai A., Okuyama T., Sugimura T. (2002). "'Chiral perturbation factor' approach reveals importance of entropy term in stereocontrol of the 2,4-pentanediol-tethered reaction". J Org Chem. 67(19):6593-8. doi: 10.1021/jo025937s.

Tangvarasittichai O., Tangvarasittichai S. (2018). "Oxidative Stress, Ocular Disease and Diabetes Retinopathy". Curr Pharm Des. 24(40):4726-4741. doi: 10.2174/1381612825666190115121531.

Umapathy A., Donaldson P., Lim J. (2013). "Antioxidant Delivery Pathways in the Anterior Eye". Biomed Research International, 10 pages. doi: 10.1155/2013/207250.

UN (2011). United Nations Globally Harmonized System of Classification and Labelling of Chemicals (GHS), ST/SG/AC.10/30 Rev 4, Part 3 Health Hazards—Chapter 3.3 Serious eye damage/eye irritation. New York & Geneva: United Nations Publications. pp. 133-144. Available: [http://www.unece.org/trans/danger/publi/ghs/ghs_rev04/04files_e.html].

Ung L., Pattamatta U., Carnt N., Wilkinson-Berka M., Liew G., White A J R. (2017). "Oxidative stress and reactive oxygen species: a review of their role in ocular disease". Clin Sci. 131(24): 2865-2883. doi: 10.1042/CS20171246.

US EPA (1998). Health Effects Test Guideline, OPPTS 870.2400 Acute Eye Irritation. EPA 712-C-98-195. US Environmental Protection Agency, Washington, DC, USA.

US EPA (2003). Label Review Manual. 3rd Edition. EPA 735-B-03-001. US Environmental Protection Agency, Washington, DC, USA.

Wang K., Hawley M C., Furney T D. (2003). "A selectivity study of 2,4-pentanediol hydrogenolysis combining experiments and computer simulation". Chemical Engineering Science. 58(18):4271-4285. doi: 10.1016/S0009-2509(03)00285-9.

Wilson S L., Ahearne M., Hopkinson A. (2015). "An overview of current techniques for ocular toxicity testing". Toxicology. 327:32-46.

Winterbourn C C. (1995). "Toxicity of iron and hydrogen peroxide: the Fenton reaction". Toxicol Lett. 82-83:969-74. doi: 10.1016/0378-4274(95)03532-x.

Zhang L., Zhang Z., He X., Zhang F., Zhang Z. (2017). "Regulation of the products of styrene oxidation". Chemical Engineering Research and Design. 120:171-178. doi: 10.1016/j.cherd.2017.02.012.

Zhu T., Lim B S., Park H C., Son K M., Yang H C. (2012). "Effects of the iron-chelating agent deferoxamine on triethylene glycol dimethacrylate, 2-hydroxyethyl methacrylate, hydrogen peroxide-induced cytotoxicity". J Biomed Mater Res B Appl Biomater. 100(1):197-205. doi: 10.1002/jbm.b.31939

What is claimed is:

1. An in vitro method for predicting ocular irritancy of a test substance and effecting a reduced false positive rate, the method comprising:
applying the test substance to an in vitro ocular irritancy test system in the presence of an antioxidant formulation, wherein the antioxidant formulation comprises ascorbic acid at about 0.27-60 mM and is added to the test system prior to applying the test substance,
measuring a test system response; and
predicting the ocular irritancy of the test substance based on the in vitro ocular irritancy test system response,
wherein the antioxidant formulation reduces the false positive rate relative to the same test performed without the antioxidant formulation.

2. The method of claim 1, wherein the test system is a biochemical test system comprising purified or semi-purified molecules.

3. The method of claim 1, wherein the test system comprises reconstituted human corneal epithelium (RhCE).

4. The method of claim 1, wherein the test system is a Depth of Injury (DoI) test system comprising excised eyes.

5. The method of claim 1, wherein the antioxidant formulation does not change the true positive rate or true negative rate.

* * * * *